US008765403B2

(12) United States Patent
Dueber et al.

(10) Patent No.: US 8,765,403 B2
(45) Date of Patent: Jul. 1, 2014

(54) USE OF SYNTHETIC SCAFFOLDS FOR THE PRODUCTION OF BIOSYNTHETIC PATHWAY PRODUCTS

(75) Inventors: John E. Dueber, Oakland, CA (US); Jay D. Keasling, Berkeley, CA (US); Gabriel C. Wu, Daly City, CA (US); Ghulam Reza Khan Malmirchegini, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 579 days.

(21) Appl. No.: 12/918,725

(22) PCT Filed: Feb. 26, 2009

(86) PCT No.: PCT/US2009/035274
§ 371 (c)(1),
(2), (4) Date: Sep. 29, 2010

(87) PCT Pub. No.: WO2009/108774
PCT Pub. Date: Sep. 3, 2009

(65) Prior Publication Data
US 2011/0008829 A1  Jan. 13, 2011

Related U.S. Application Data

(60) Provisional application No. 61/032,308, filed on Feb. 28, 2008.

(51) Int. Cl.
| | | |
|---|---|---|
| *C12P 1/00* | (2006.01) | |
| *C12P 7/00* | (2006.01) | |
| *C07H 21/00* | (2006.01) | |
| *C12N 1/21* | (2006.01) | |
| *C12N 5/10* | (2006.01) | |
| *C12N 9/00* | (2006.01) | |
| *C12P 21/00* | (2006.01) | |

(52) U.S. Cl.
USPC ............ 435/41; 435/132; 435/69.1; 435/183; 435/252.3; 435/325; 536/23.1; 536/23.2

(58) Field of Classification Search
USPC ....................... 435/69.1, 320.1, 183; 530/350; 536/23.1, 23.2
See application file for complete search history.

(56) References Cited

U.S. PATENT DOCUMENTS

| 6,969,584 B2 | 11/2005 | Nolan et al. | |
|---|---|---|---|
| 2002/0137891 A1* | 9/2002 | Hill et al. ...................... | 530/350 |
| 2006/0110789 A1 | 5/2006 | Gokhale | |

FOREIGN PATENT DOCUMENTS

WO   WO 2005/010198   2/2005

OTHER PUBLICATIONS

Wang et al., Journal of Biotechnology 157:258-260, 2012.*
Bishop et al., "Rho GTPases and Their Effector Proteins", 2000, Biochem J., 348:241-255.
Dueber et al., "Reprogramming Control of an Allosteric Signaling Switch Through Modular Recombination", (2003) Science 301:1904-1908.
Dueber et al., "Rewiring Cell Signaling: the Logic and Plasticity of Eukaryotic Protein Circuitry", 2004, Current Opinion in Structural Biology, 14:690-699.
Dueber et al., "Synthetic Protein Scaffolds Provide Modular Control Over Metabolic Flux", Aug. 2009, Nature Biotechnology, 27(8):753-759.
Garrard et al., "Structure of Cdc42 in a Complex with the GTPase-binding Domain of the Cell Polarity Protein, Par6", 2003, The EMBO Journal, 22(5):1125-1133.
Miller et al., "Ligand-regulated Peptide Aptamers that Inhibit the 5'AMP-activated Protein Kinase", 2007, J. Mol. Biol., 365:945-957.
Park et al, "The Shank Family of Postsynaptic Density Proteins Interact with and Promotes Synaptic Accumulation of the βPIX Guanine Nucleotide Exchange Factor for Rac1 and Cdc42", 2003, The Journal of Biological Chemistry, 278(21):19220-19229.
Pawson et al., "Oncognic Re-wiring of Cellular Signaling Pathways", 2007, Oncogene, 26:1268-1275.
Sallee el al., "Engineering Modular Protein Interaction Switches by Sequence Overlap", 2007, J. Am. Chem. Soc., 129:4606-4611.
Yoon et al., "Combinatorial Expression of Bacterial Whole Mevalonate Pathway for the Production of β-carotene in *E. coli* ", available on line at Jan. 2009, Journal of Biotechnology. 140:218-226.
Yoon et al., "Enhanced Lycopene Production in *Escherichia coli* Engineered to Synthesize Isopentenyl Diphosphate and Dimethylally Diphosphate From Mevalonate", Aug. 20, 2006, Biotechnology and Bioenginering. 94(6):1025-1032.
Yoon et al., "Increased β-Carotene Production in Recombinant *Escherichia coli* Harboring an Engineered Isoprenoid Precursor Pathway with Mevalonate Addition", 2007, Biotechnol. Prog., 23:599-605.
Bulow, et al., "Multienzyme Systems Obtained by Gene Fusion", Trends in Biotechnology, 1991, vol. 9, No. 1, pp. 226-231.
Chang, et al. "Production of Isoprenoid Pharmaceuticals by Engineered Microbes", Nature Chemical Biology, 2006, vol. 2, No. 12, pp. 674-681.
Conrado, et al., "Engineering the Spatial Organization of Metabolic Enzymes: Mimicking Nature's Synergy", Current Opinion in Biotechnology, 2008, vol. 19, No. 5, pp. 492-499.
Fierobe H-P, et al., "Degradation of Cellulose Substrates by Cellulosome Chimeras-Substrate Targeting Versus Proximity of Enzyme Components", Journal of Biological Chemistry, 2002, vol. 277, No. 51, pp. 49621-49630.

(Continued)

*Primary Examiner* — Delia Ramirez
(74) *Attorney, Agent, or Firm* — Paula A. Borden; Bozicevic, Field & Francis LLP

(57) ABSTRACT

The present invention provides methods of producing a product or product precursor of a biosynthetic pathway in a genetically modified host cell. The present invention also provides genetically modified host cells comprising nucleic acids encoding a scaffold polypeptide and nucleic acids comprising nucleotide sequences encoding two or more enzymes in a biosynthetic pathway. The present invention further provides nucleic acids comprising nucleotide sequences encoding scaffold polypeptides, for use in a subject method.

7 Claims, 16 Drawing Sheets

(56) References Cited

OTHER PUBLICATIONS

Fierobe H-P, et al., "Action of Designer Cellulosomes on Homogeneous Versus Complex Substrates", Journal of Biological Chemistry, 2005, vol. 280, No. 16, pp. 16325-16334.

Gokhale, et al., "Role of Linkers in Communication Between Protein Modules", Current Opinion in Chemical Biology, 2000, vol. 4, pp. 22-27.

Khosla, et al. "Modular Enzymes", Nature: International Weekly Journal of Science, 2001, vol. 409, pp. 247-252.

Pitera, et al. "Balancing a Heterologous Mevalonate Pathway for Improved Isoprenoid Production in *Escherichia coli* ", Metabolic Engineering, 2007, vol. 9, No. 2, pp. 193-207.

Tsuji, et al. "Selective Protein-Protein Interactions Direct Channeling of Interactions Direct Channeling of Intermediates Between Polyketide Synthase Modules +", Biochemistry, 2001, vol. 40, No. 8, pp. 2326-2331.

* cited by examiner

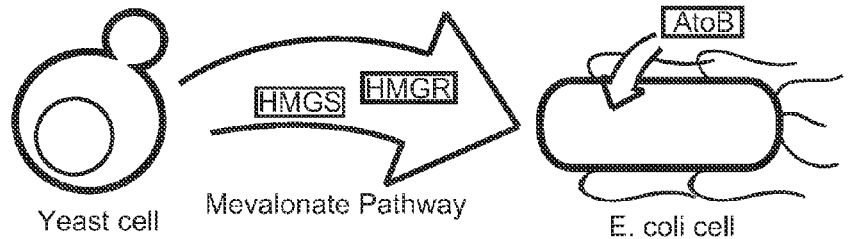
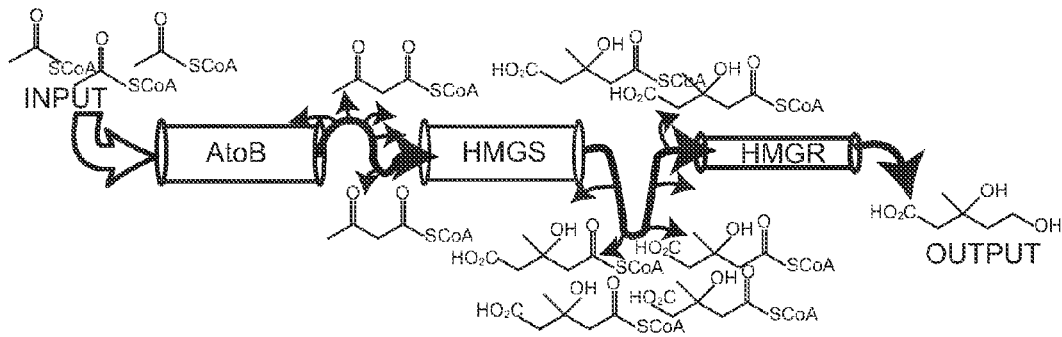
FIG. 1a
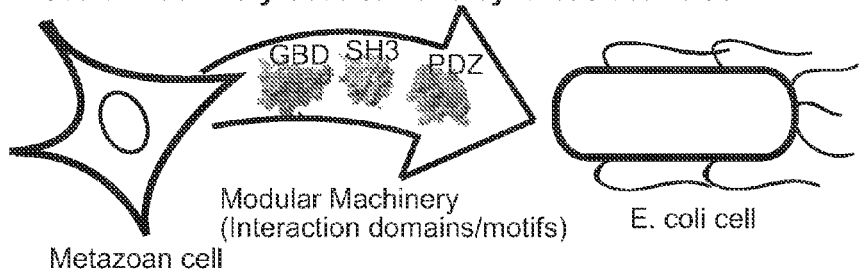
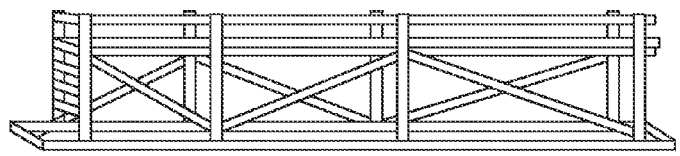
FIG. 1b

AtoB (acetoacetyl-CoA thiolase)-linker-GBD ligand
```
  1 M K N C V I V S A V R T A I G S F N G S L A S T S  25
 26 A I D L G A T V I K A A I E R A K I D S Q H V D E  50
 51 V I M G N V L Q A G L G Q N P A R Q A L L K S G L  75
 76 A E T V C G F T V N K V C G S G L K S V A L A A Q  100
101 A I Q A G Q A Q S I V A G G M E N M S L A P Y L L  125
126 D A K A R S G Y R L G D G Q V Y D V I L R D G L M  150
151 C A T H G Y H M G I T A E N V A K E Y G I T R E M  175
176 Q D E L A L H S Q R K A A A I E S G A F T A E I    200
201 V P V N V V T R K K T F V F S Q D E F P K A N S T  225
226 A E A L G A L R P A F D K A G T V T A G N A S G I  250
251 N D G A A A L V I M E E S A A L A A G L T P L A R  275
276 I K S Y A S G G V P P A L M G M G P V P A T Q K A  300
301 L Q L A G L Q L A D I D L I E A N E A F A A Q F L  325
326 A V G K N L G F D S E K V N V N G G A I A L G H P  350
351 I G A S G A R I L V T L L H A M Q A R D K T L G L  375
376 A T L C I G G G Q G I A M V I E R L N P R G S G S  400
401 G L V G A L M H V M Q K R S R A I H S S D E G E D  425
426 Q A G D E D E D *
```

HMG CoA Synthase-linker-SH3 ligand
```
  1 M K L S T K L C W C G I K G R L R P Q K Q Q Q L H  25
 26 N T N L Q M T E L K K Q K T A E Q K T R P Q N V G  50
 51 I K G I Q I Y I P T Q C V N Q S E L E K F D G V S  75
 76 Q G K Y T I G L G Q T N M S F V N D R E D I Y S M  100
101 S L T V L S K L I K S Y N I D T N K I G R L E V G  125
126 T E T L I D K S K S V K S V L M Q L F G E N T D V  150
151 E G I D T L N A C Y G G T N A L F N S L N W I E S  175
176 N A W D G R D A I V V C G D I A I Y D K G A A R P  200
201 T G G A G T V A M W I G P D A P I V F D S V R A S  225
226 Y M E H A Y D F Y K P D F T S E Y P Y V D G H F S  250
251 L T C Y V K A L D Q V Y K S Y S K K A I S K G L V  275
276 S D P A G S D A L N V L K Y F D Y N V F H V P T C  300
301 K L V T K S Y G R L L Y N D F R A N P Q L F P E V  325
326 D A E L A T R D Y D E S L T D K N I E K T F V N V  350
351 A K P F H K E R V A Q S L I V P T N T G N M Y T A  375
376 S V Y A A F A S L L N Y V G S D D L Q G K R V G L  400
401 F S Y G S G L A A S L Y S C K I V G D V Q H I I K  425
426 E L D I T N K L A K R I T E T P K D Y E A A I E L  450
451 R E N A H L K K N F K P Q G S I E H L Q S G V Y Y  475
476 L T N I D D K F R R S Y D V K K L E G S G S G S G  500
501 S G P P P A L P P K R R R P G *
```

FIG. 4A

HMG CoA Reductase-linker-PDZ ligand

Scaffold (X1=GBD)$_1$(Y1)(X2=SH3)$_1$(Y2)(X3=PDZ)$_1$

Scaffold (X1=GBD)₁(Y1)(X2=SH3)₂(Y2)(X3=PDZ)₂

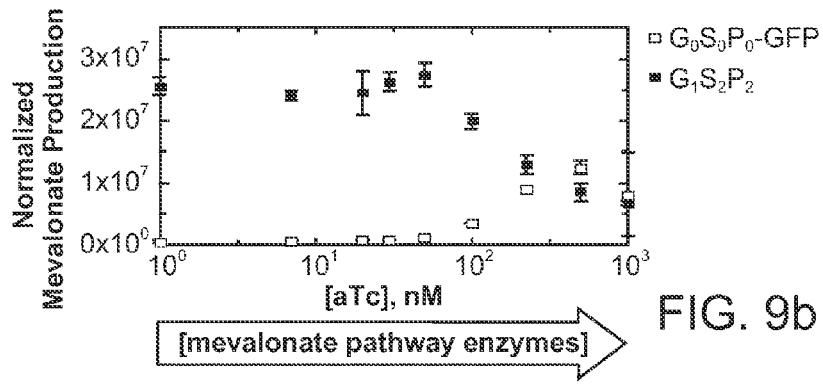
FIG. 9b
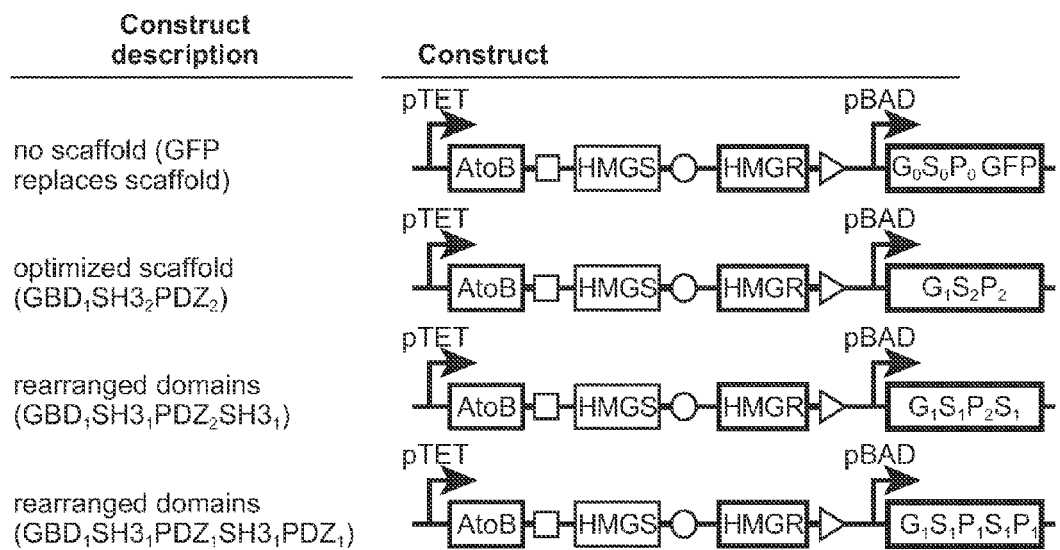
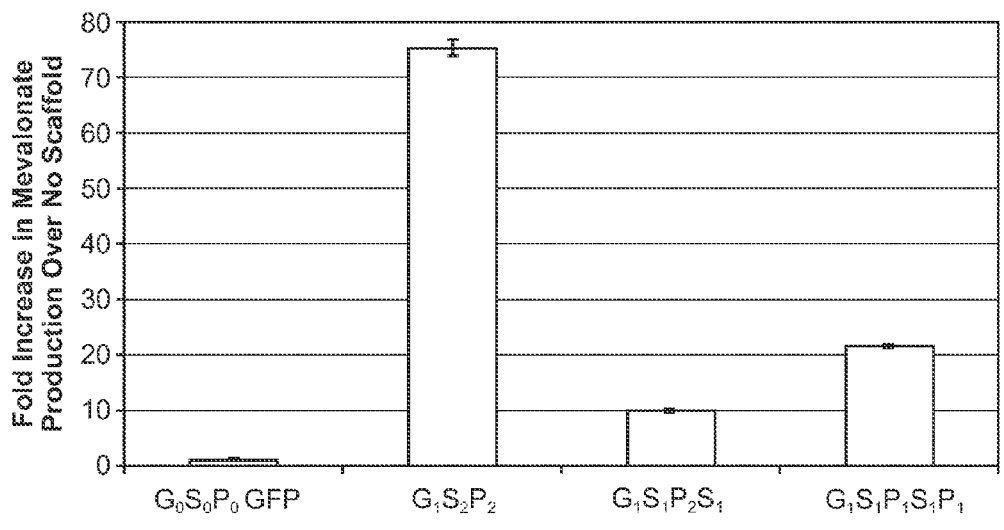
FIG. 10

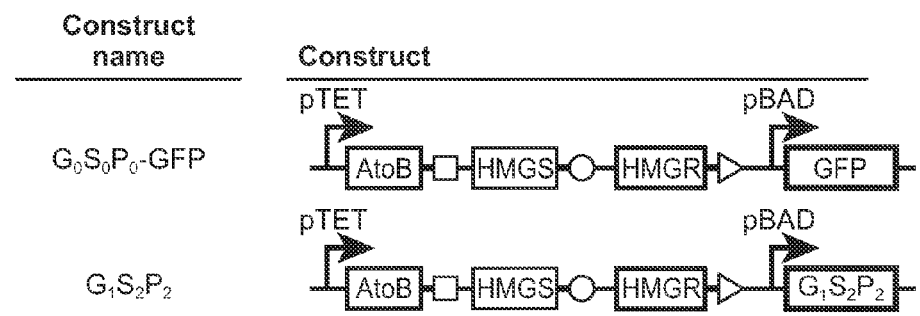
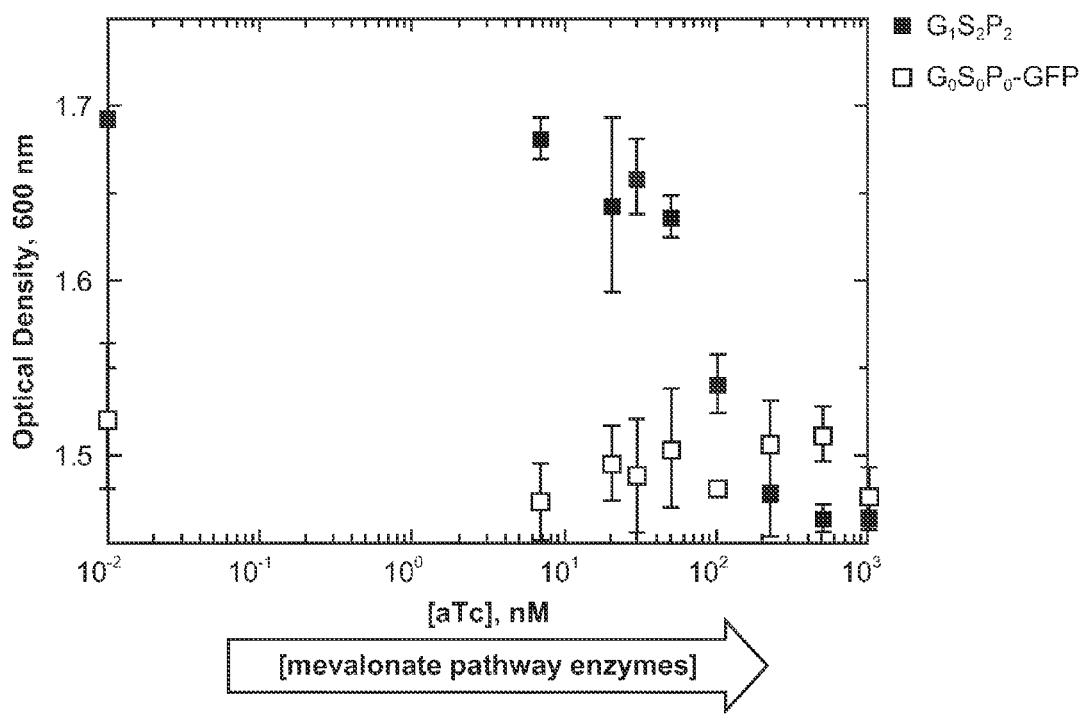
FIG. 12

US 8,765,403 B2

USE OF SYNTHETIC SCAFFOLDS FOR THE PRODUCTION OF BIOSYNTHETIC PATHWAY PRODUCTS

CROSS-REFERENCE

This application claims the benefit of U.S. Provisional Patent Application No. 61/032,308, filed Feb. 28, 2008, which application is incorporated herein by reference in its entirety.

STATEMENT REGARDING FEDERALLY SPONSORED RESEARCH

This invention was made with government support under Grant No. EEC-0540879 awarded by the National Science Foundation. The government has certain rights in the invention.

BACKGROUND

Biosynthetic pathways are engineered to produce high yields of desired products. Engineered biosynthetic pathways employ multiple enzymes, often heterologous to the expression host. The enzymes often produce metabolites foreign to the host, thus resulting in side effects such as flux imbalances, toxicity from metabolite intermediates, and/or a burden from protein overexpression. Protein expression levels may be modulated via plasmid copy numbers and promoter strengths. However, combinatorial titration of individual enzyme expression levels is experimentally tedious, especially for multi-enzyme pathways.

There is a need in the art for efficient methods of producing products of biosynthetic pathways.

Literature

U.S. Pat. No. 6,969,584; Dueber et al. (2003) *Science* 301: 1904; WO 2005/01098

SUMMARY OF THE INVENTION

The present invention provides methods of producing a product or product precursor of a biosynthetic pathway in a genetically modified host cell. The present invention also provides genetically modified host cells comprising nucleic acids encoding a scaffold polypeptide and nucleic acids comprising nucleotide sequences encoding two or more enzymes in a biosynthetic pathway. The present invention further provides nucleic acids comprising nucleotide sequences encoding scaffold polypeptides, for use in a subject method.

BRIEF DESCRIPTION OF THE DRAWINGS

FIGS. 1A-C provide schematic depictions of unregulated biosynthetic pathway enzymes (FIG. 1A), modular machinery used to build synthetic scaffolds (FIG. 1B), and use of scaffolding to balance biosynthetic pathway flux and increase efficiency (FIG. 1C).

FIGS. 4A and 4B provide amino acid sequences of chimeric mevalonate pathway enzymes. Linker sequences are underlined; and heterologous peptide ligands are in bold text. FIG. 3A provides an ato-B-linker-GBD ligand amino acid sequence (SEQ ID NO:33) and an HMG CoA synthase-linker-SH3 ligand amino acid sequence (SEQ ID NO:34). FIG. 3B provides HMG CoA reductase-linker-PDZ ligand amino acid sequence (SEQ ID NO:35).

Figure 5A:
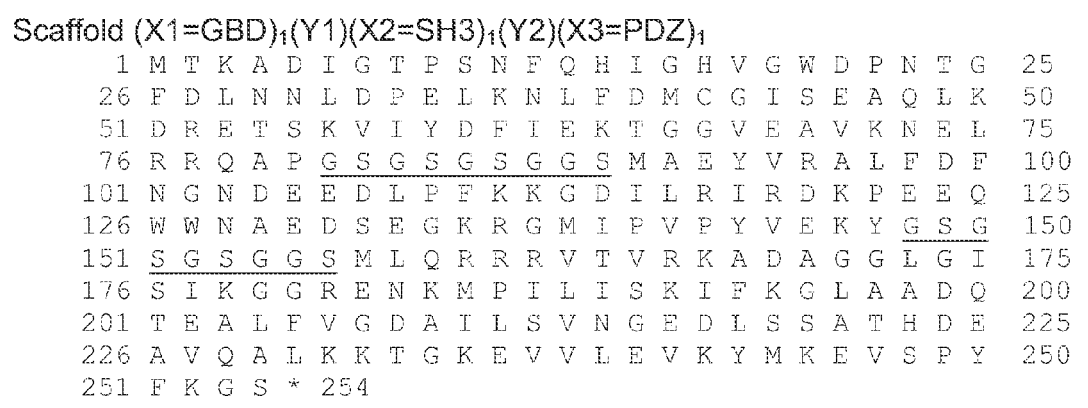
Figure 5B:
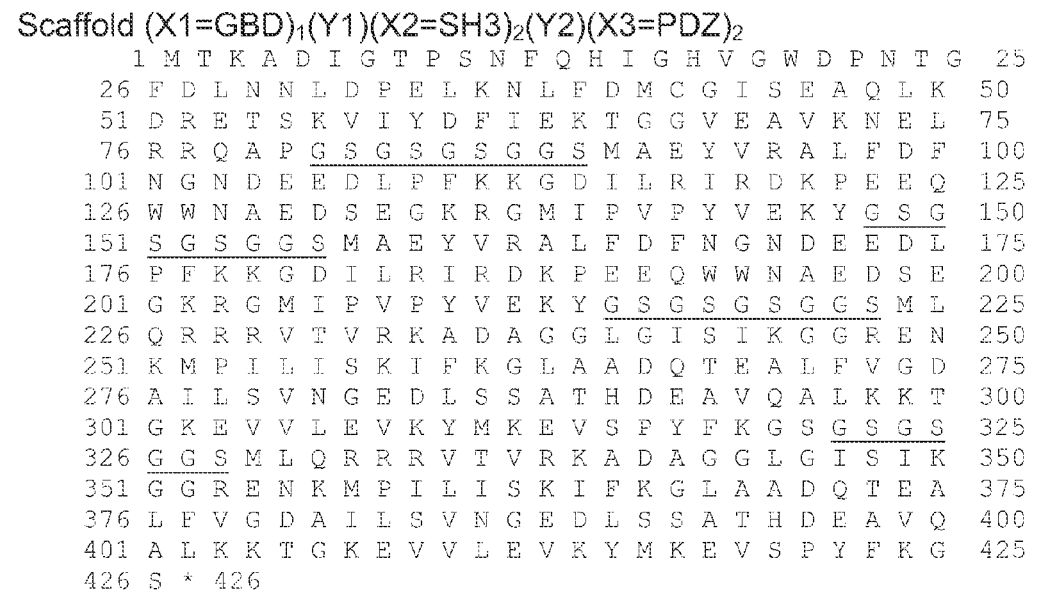

FIGS. 5A and 5B provide amino acid sequences of exemplary scaffolds. Linker peptides are underlined. FIG. 5A provides an exemplary Scaffold $(X1=GBD)_1(Y1)(X2=SH3)_1(Y2)(X3=PDZ)_1$ amino acid sequence (SEQ ID NO:36). FIG. 5B provides an exemplary $(X1=GBD)_1(Y1)(X2=SH3)_2(Y2)(X3=PDZ)_2$ amino acid sequence (SEQ ID NO:37).

FIGS. 9A and 9B depict dependence of scaffold in enhancement of mevalonate production.

FIG. 10 depicts the effect of domain rearrangements in scaffold architecture on pathway flux.

FIG. 12 depicts cell density at saturation for scaffolded pathway at low induction of pathway enzymes and at high expression of pathway enzymes.

DEFINITIONS

Figure 1C:
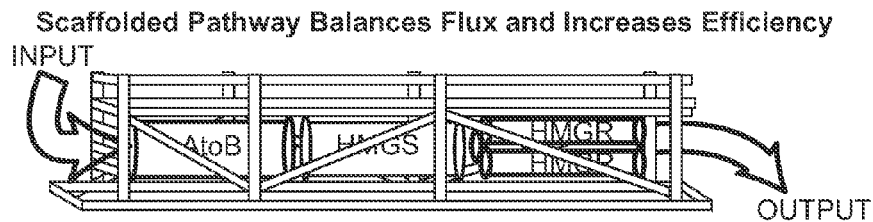

The terms "nucleic acid," used herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "heterologous," as used herein in the context of a genetically modified host cell, refers to a polypeptide wherein at least one of the following is true: (a) the polypeptide is foreign ("exogenous") to (i.e., not naturally found in) the host cell; (b) the polypeptide is naturally found in (e.g., is "endogenous to") a given host microorganism or host cell but is either produced in an unnatural (e.g., greater than expected or greater than naturally found) amount in the cell, or differs in nucleotide sequence from the endogenous nucleotide sequence such that the same encoded protein (having the same or substantially the same amino acid sequence) as found endogenously is produced in an unnatural (e.g., greater than expected or greater than naturally found) amount in the cell.

The term "heterologous," as used herein in the context of a chimeric polypeptide, refers to two components that are defined by structures derived from different sources. For example, where "heterologous" is used in the context of a chimeric polypeptide (e.g., a chimeric biosynthetic pathway enzyme), the chimeric polypeptide includes operably linked amino acid sequences that can be derived from different polypeptides (e.g., a first amino acid sequence from a biosynthetic pathway enzyme; and a second amino acid sequence that is not normally found associated with the biosynthetic pathway enzyme in nature, e.g., a peptide that binds a peptide binding element such as a PDZ domain, a GBD, an SH3 domain, etc.). Similarly, "heterologous" in the context of a polynucleotide encoding a chimeric polypeptide includes operably linked nucleotide sequences that can be derived from different coding regions (e.g., a first nucleotide sequence encoding a biosynthetic pathway enzyme; and a second nucleotide sequence encoding a peptide that is not normally found associated with the biosynthetic pathway enzyme in nature, e.g., a peptide that binds a peptide binding element such as a PDZ domain, a GBD, an SH3 domain, etc.). Other exemplary "heterologous" nucleic acids include expression constructs in which a nucleic acid comprising a coding sequence is operably linked to a regulatory element (e.g., a promoter) that is not normally associated with the coding sequence (e.g., to provide for expression in a host cell of interest, to provide for higher or lower levels of the encoded protein, etc.). For example, a T7 promoter operably linked to a polynucleotide encoding a chimeric biosynthetic pathway enzyme is said to be heterologous to the coding sequence for the chimeric biosynthetic pathway enzyme.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "genetically modified host cell" (also referred to as a "recombinant host cell") is a host cell into which has been introduced a heterologous nucleic acid, e.g., an expression vector. For example, a prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The terms "isoprenoid," "isoprenoid compound," "terpene," "terpene compound," "terpenoid," and "terpenoid compound" are used interchangeably herein, and refer to any compound that is capable of being derived from isopentenyl pyrophosphate (IPP). The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, diterpenes, triterpenes, sesquiterpenes, and polyterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid precursor compound is produced. The term "terpene synthase" includes enzymes that catalyze the conversion of a prenyl diphosphate into an isoprenoid or isoprenoid precursor.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The mevalonate pathway is illustrated schematically in FIG. 7. The "top half" of the mevalonate pathway refers to the enzymes responsible for the conversion of acetyl-CoA to mevalonate.

Figure 8:
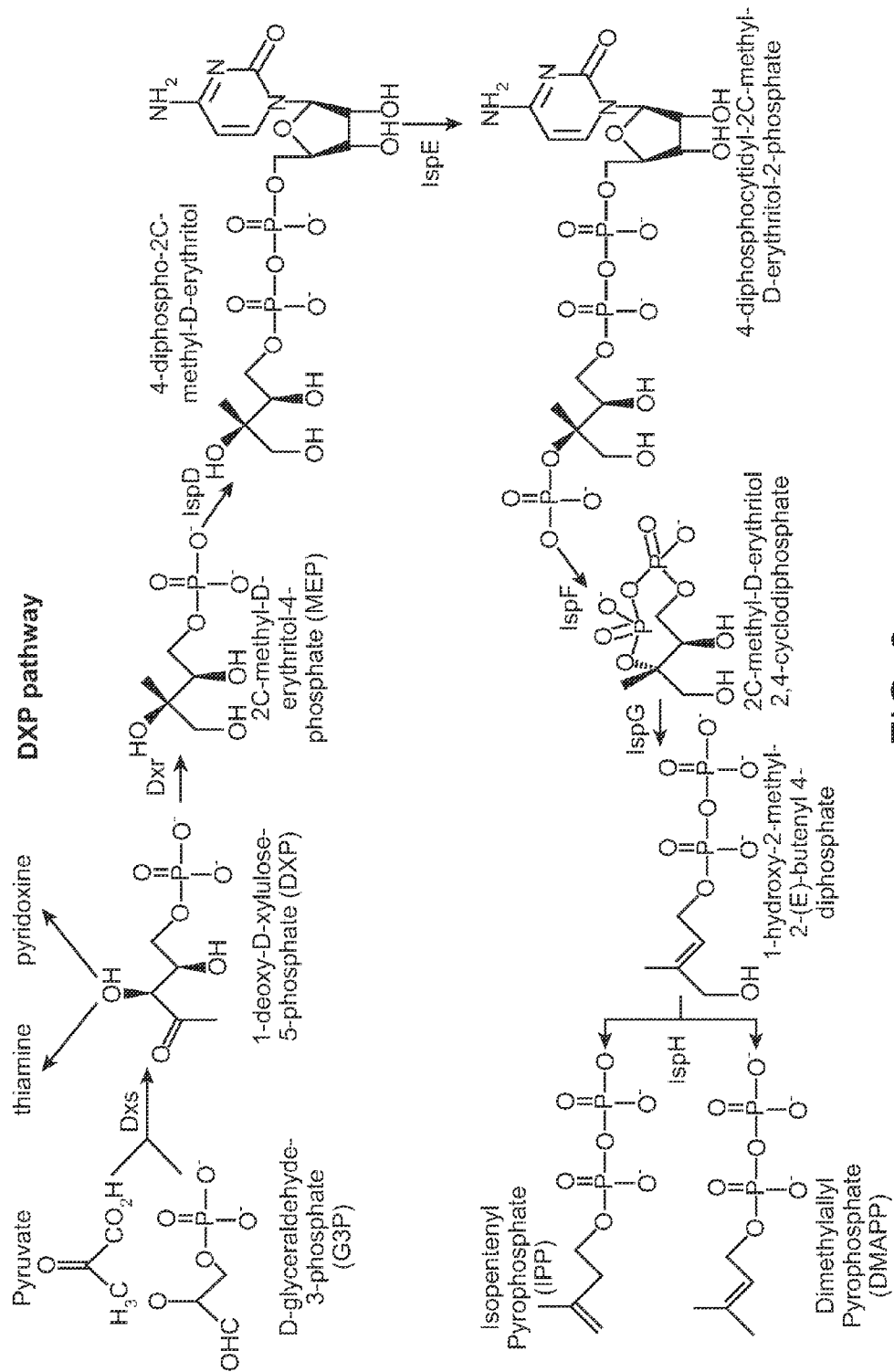
FIG. 8 is a schematic representation of the DXP pathway for the production of IPP and dimethylallyl pyrophosphate (DMAPP).

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate, where DXP pathway comprises enzymes that catalyze the reactions depicted schematically in FIG. 8. Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an enzyme" includes a plurality of such enzymes and reference to "the scaffold polypeptide" includes reference to one or more scaffold polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of producing a product or product precursor of a biosynthetic pathway in a genetically modified host cell. The present invention also provides genetically modified host cells comprising nucleic acids encoding a scaffold polypeptide and nucleic acids comprising nucleotide sequences encoding two or more enzymes in a biosynthetic pathway. The present invention further provides nucleic acids comprising nucleotide sequences encoding scaffold polypeptides, for use in a subject method.

Methods of Producing a Product or Product Precursor of a Biosynthetic Pathway

The present invention provides methods of producing a product or product precursor of a biosynthetic pathway in a genetically modified host cell. The methods generally involve culturing a genetically modified host cell under suitable conditions, wherein the genetically modified host cell comprises: a) a nucleic acid comprising a nucleotide sequence encoding a scaffold polypeptide comprising at least two different peptide binding elements; and b) one or more nucleic acids comprising nucleotide sequences encoding two or more enzymes in a biosynthetic pathway, where the biosynthetic pathway enzymes are chimeric, e.g., a chimeric biosynthetic pathway enzyme comprises a heterologous peptide that binds to a peptide binding element in the scaffold polypeptide. A given peptide binding element binds a particular heterologous peptide present within a chimeric biosynthetic pathway enzyme, thereby providing for association of the chimeric biosynthetic pathway enzymes with the scaffold polypeptide. The association of the chimeric biosynthetic pathway enzymes with the scaffold polypeptide is of sufficient affinity that the chimeric biosynthetic pathway enzymes are immobilized on the scaffold polypeptide. Biosynthetic pathway enzymes that are "adjacent to" one another in a biosynthetic pathway, i.e., that act on a product of an immediately preceding enzyme in the pathway, or that product a product that is a substrate for an immediately downstream enzyme in the pathway, are immobilized spatially relative to one another in the same order as they act in a biosynthetic pathway. The cells are cultured such that a substrate for the first enzyme in the biosynthetic pathway is present in the cell; the biosynthetic pathway enzymes are synthesized in the cell and convert the substrate into a product.

Use of a scaffold polypeptide to immobilize biosynthetic pathway enzymes provides for one or more of the following: 1) increased efficiency of pathway flux; 2) optimized metabolic flux through the pathway; 3) reduced metabolic burden on the host cell; and 4) reduced concentration of potentially toxic free intermediates in the cytosol/cytoplasm. Balance of enzyme activity levels is achieved through use of a scaffold polypeptide. For example, the copy number of an enzyme having lower activity that is recruited to a scaffold can be higher than the copy number of an enzyme having higher activity. This can be advantageous, e.g., where the lower activity enzyme catalyzes a rate-limiting step in the pathway. Use of a scaffold polypeptide increases efficiency and optimizes pathway flux; because of increased efficiency and optimized flux, equivalent or higher yields of product can be achieved with lower levels of enzyme. Lower levels of enzyme production in a host cell are advantageous, as it places less of a metabolic burden on the host cell. Because the turnover of biosynthetic pathway intermediates is more efficient with use of a scaffold polypeptide, the amount/concentration of pathway intermediates free in the cytosol or cytoplasm is reduced. Reduced levels of free pathway intermediates are advantageous where such intermediates are toxic to the host cell.

Co-localization of a first enzyme and a second enzyme in a biosynthetic pathway can also be achieved by incorporating into the first and second enzymes heterologous binding elements that bind to one another and thereby bring the enzymes into spatial proximity. Heterologous binding elements include a "heterologous peptide" and a "peptide binding element," where a "heterologous peptide" is a ligand for a "peptide binding element." Thus, e.g., a first biosynthetic pathway enzyme can comprise a first heterologous binding element (e.g., a peptide binding element, as described below), and a second biosynthetic pathway enzyme can comprise a second heterologous binding element (e.g., a heterologous peptide, as described below), where the second heterologous binding element is a ligand for the first binding element, where the first enzyme produces a product that is a substrate for the second enzyme, and where binding of the first heterologous binding element to the second heterologous binding element brings the first and second enzymes into spatial proximity to one another.

In some embodiments, at least a first chimeric biosynthetic pathway enzyme and a second chimeric biosynthetic pathway enzyme are immobilized onto a scaffold polypeptide. The first chimeric biosynthetic pathway enzyme produces a first product that is a substrate for the second chimeric biosynthetic pathway enzyme. The second chimeric biosynthetic pathway enzyme is immobilized onto the scaffold polypeptide such that it is positioned adjacent to or very close to the first chimeric biosynthetic pathway enzyme. In this way, the effective concentration of the first product is high, and the second chimeric biosynthetic pathway enzyme can act efficiently on the first product. As an example, a scaffold polypeptide has immobilized thereon, in order from amino terminus to carboxyl terminus of the scaffold polypeptide: a) the first chimeric biosynthetic pathway enzyme; and b) the second chimeric biosynthetic pathway enzyme.

Two or more copies (e.g., two, three, four, five, six, seven, eight, nine, or ten, or more, molecules) of each enzyme can be immobilized onto the scaffold polypeptide. For example, in some embodiments, a scaffold polypeptide has immobilized thereon, in order from amino terminus to carboxyl terminus of the scaffold polypeptide: a) one molecule (copy) of the first chimeric biosynthetic pathway enzyme; and b) one molecule of the second chimeric biosynthetic pathway enzyme. In other embodiments, a scaffold polypeptide has immobilized thereon, in order from amino terminus to carboxyl terminus of the scaffold polypeptide: a) one molecule of the first chimeric biosynthetic pathway enzyme; and b) two or more molecules (e.g., two, three, four, five, six, or more, molecules) of the second chimeric biosynthetic pathway enzyme.

Two or more molecules (e.g., two, three, four, five, six, seven, eight, nine, or ten, or more, molecules) of each enzyme can be immobilized onto the scaffold polypeptide. In this way, the ratio of any given enzyme in a biosynthetic pathway to any other enzyme in the biosynthetic pathway can be varied. For example, the ratio of a first chimeric biosynthetic pathway enzyme to a second chimeric biosynthetic pathway enzyme can be varied. For example, the ratio of a first chimeric biosynthetic pathway enzyme to a second chimeric biosynthetic pathway enzyme can be varied from about 0.1:10 to about 10:0.1, e.g., from about 0.1:10 to about 0.5:10, from about 0.5:10 to about 1.0:10, from about 1.0:10 to about 2:10, from about 2:10 to about 5:10, from about 5:10 to about 7:10, from about 7:10 to about 10:10, from about 10:7 to about 10:5, from about 10:5 to about 10:2, from about 10:2 to about 10:1, from about 10:1 to about 10:0.5, or from about 10:0.5 to about 10:1. The ratio of a first chimeric biosynthetic pathway enzyme to a second chimeric biosynthetic pathway enzyme can be varied from about 1:5 to about 5:1, e.g., from about 1:5 to about 2:5, from about 2:5 to about 3:5, from about 3:5 to about 5:5, from about 5:5 to about 5:3, from about 5:3 to about 5:2, or from about 5:2 to about 5:1.

In some embodiments, at least three chimeric biosynthetic pathway enzymes are immobilized onto a scaffold polypeptide. The first chimeric biosynthetic pathway enzyme produces a first product that is a substrate for the second chimeric biosynthetic pathway enzyme, and the second chimeric biosynthetic pathway enzyme produces a second product that is a substrate for the third chimeric biosynthetic pathway enzyme. In these embodiments, a scaffold polypeptide has immobilized thereon, in order from amino terminus to carboxyl terminus of the scaffold polypeptide: a) the first chimeric biosynthetic pathway enzyme; b) the second chimeric biosynthetic pathway enzyme; and c) the third biosynthetic pathway enzyme.

In some embodiments, at least four chimeric biosynthetic pathway enzymes are immobilized onto a scaffold polypeptide. The first chimeric biosynthetic pathway enzyme produces a first product that is a substrate for the second chimeric biosynthetic pathway enzyme, the second chimeric biosynthetic pathway enzyme produces a second product that is a substrate for the third chimeric biosynthetic pathway enzyme, and the third chimeric biosynthetic pathway enzyme produces a product that is a substrate for the fourth chimeric biosynthetic pathway enzyme. In these embodiments, a scaffold polypeptide has immobilized thereon, in order from amino terminus to carboxyl terminus of the scaffold polypeptide: a) the first chimeric biosynthetic pathway enzyme; b) the second chimeric biosynthetic pathway enzyme; c) the third chimeric biosynthetic pathway enzyme; and d) the chimeric fourth biosynthetic pathway enzyme.

In some embodiments, at least five chimeric biosynthetic pathway enzymes are immobilized onto a scaffold polypeptide. The first chimeric biosynthetic pathway enzyme produces a first product that is a substrate for the second chimeric biosynthetic pathway enzyme, the second chimeric biosynthetic pathway enzyme produces a second product that is a substrate for the third chimeric biosynthetic pathway enzyme, the third chimeric biosynthetic pathway enzyme produces a product that is a substrate for the fourth chimeric biosynthetic pathway enzyme, and the fourth chimeric biosynthetic pathway enzyme produces a product that is a substrate for the fifth chimeric biosynthetic pathway enzyme. In these embodiments, a scaffold polypeptide has immobilized thereon, in order from amino terminus to carboxyl terminus of the scaffold polypeptide: a) the first chimeric biosynthetic pathway enzyme; b) the second chimeric biosynthetic pathway enzyme; c) the third chimeric biosynthetic pathway enzyme; d) the fourth chimeric biosynthetic pathway enzyme; and e) the fifth chimeric biosynthetic pathway enzyme. It will be apparent from these examples that a sixth, seventh, eighth, ninth, tenth, etc., biosynthetic pathway enzyme can be immobilized onto a scaffold polypeptide, that the enzymes are immobilized spatially in the order in which they function in a pathway, and that each enzyme can be immobilized onto the scaffold polypeptide in one two, three, four, five, six, seven, eight, nine, ten, or more copies (or molecules).

Scaffold Polypeptide

A scaffold polypeptide is designed to organize biosynthetic pathway enzymes into a functional complex. A scaffold polypeptide comprises two or more peptide binding elements (PBEs). Binding of the PBE to a heterologous peptide (HP) present in a chimeric biosynthetic pathway enzyme provides for immobilization of enzyme on the scaffold polypeptide. Each PBE is capable of binding a corresponding HP present in a chimeric biosynthetic pathway enzyme. The binding between a PBE and HP is via protein-protein interaction. A given PBE can be immediately adjacent to another PBE, or can be separated from an adjacent PBE through a linker. The scaffold polypeptide can be introduced to a variety of different types of host cells, e.g., by introducing into a host cell a nucleic acid comprising a nucleotide sequence encoding the scaffold polypeptide.

A scaffold polypeptide comprises at least two different PBEs, thus binding at least two corresponding HPs in at least two different chimeric enzymes. A scaffold polypeptide can provide binding of 2 to 25 enzymes, thus immobilizing the enzymes on the scaffold. For example, a scaffold polypeptide can bind from 2 enzymes to 3 enzymes, from 3 enzymes to 6 enzymes, from 6 enzymes to 10 enzymes, from 10 enzymes to 15 enzymes, from 15 enzymes to 20 enzymes, or from 20 enzymes to 25 enzymes.

A scaffold polypeptide has one, two or more copies of each PBE. For example, a scaffold polypeptide can have from 1 copy to 10 copies of each PBE, e.g., a scaffold polypeptide can comprise one, two, three, four, five, six, seven, eight, nine, ten, or more, copies of each PBE. Each PBE can independently be present in one or more copies. The copies can be in tandem, or separated by a linker. For example, a scaffold may comprise one copy of a first PBE ($PBE_1$), two copies of $PBE_2$, and three copies of $PBE_3$, where the copies are in tandem, or are separated by a linker.

A scaffold polypeptide has a general formula of $[(X)_n(Y)]_m$, where each X is a different peptide binding element, wherein n is an integer from one to about 10 (e.g., where n is 1, 2, 3, 4, 5, 6, 7, 8, 9, or 10), where Y, if present, is a linker peptide, and where m is an integer from 2 to about 50 (e.g., from 2 to about 3, from 3 to about 6, from 6 to about 10, from 10 to about 15, from 15 to 20, from 20 to 25, from 25 to 30, from 30 to 35, from 35 to 40, from 40 to 45, or from 45 to 50).

For example, in some embodiments, a scaffold polypeptide has the formula $(X_1)_{n1}(Y_1)(X_2)_{n2}(Y_2)(X_3)_{n3}$, where $X_1$ is a first PBE that provides for binding of a first chimeric biosynthetic pathway enzyme; where $X_2$ is a second PBE that provides for binding of a second chimeric biosynthetic pathway enzyme; where $X_3$ is a third PBE that provides for binding of a third chimeric biosynthetic pathway enzyme; where each of $n_1$, $n_2$, and $n_3$ is independently an integer from one to about 10; and where each Y, if present, is a linker peptide. As another example, in some embodiments, a scaffold polypeptide has the formula $(X_1)_{n1}(Y_1)(X_2)_{n2}(Y_2)(X_3)_{n3}(X_4)_{n4}(Y_4)(X_5)_{n5}(Y_5)(X_6)_{n6}$, where $X_1$ is a first PBE that provides for binding of a first chimeric biosynthetic pathway enzyme; where $X_2$ is a second PBE that provides for binding of a second chimeric biosynthetic pathway enzyme; where $X_3$ is a third PBE that provides for binding of a third chimeric biosynthetic pathway enzyme; $X_4$ is a fourth PBE that provides for binding of a fourth chimeric biosynthetic pathway enzyme; where $X_5$ is a fifth PBE that provides for binding of a fifth chimeric biosynthetic pathway enzyme; where $X_6$ is a sixth PBE that provides for binding of a sixth chimeric biosynthetic pathway enzyme; where each of $n_1$, $n_2$, $n_3$, $n_4$, $n_5$, and $n_6$ is independently an integer from one to about 10; and where each Y, if present, is a linker peptide.

In some embodiments, a scaffold polypeptide has the formula $(X_1)(Y_1)(X_2)_2(Y_2)(X_3)_2(Y_3)$, where $X_1$ is a first PBE that provides for binding of a first chimeric biosynthetic pathway enzyme and is present in one copy; where $X_2$ is a second PBE that provides for binding of a second chimeric biosynthetic pathway enzyme and is present in two copies; where $X_3$ is a third PBE that provides for binding of a third chimeric biosynthetic pathway enzyme and is present in two copies; and where each Y, if present, is a linker peptide. In another example, in some embodiments, a scaffold polypeptide has the formula $(X_1)(Y_1)(X_2)_2(Y_2)(X_3)_4(Y_3)(X_4)(Y_4)(X_5)(Y_5)(X_6)(Y_6)$, where $X_1$ is a first PBE that provides for binding of a first chimeric biosynthetic pathway enzyme and present in one copy; where $X_2$ is a second PBE that provides for binding of a second chimeric biosynthetic pathway enzyme and present in two copies; where $X_3$ is a third PBE that provides for binding of a third chimeric biosynthetic pathway enzyme and present in four copies; $X_4$ is a fourth PBE that provides for binding of a fourth chimeric biosynthetic pathway enzyme and present in one copy; where $X_5$ is a fifth PBE that provides for binding of a fifth chimeric biosynthetic pathway enzyme and present in one copy; where $X_6$ is a sixth PBE that provides for binding of a sixth chimeric biosynthetic pathway enzyme and present in one copy; and where each Y, if present, is a linker peptide.

A PBE can have a length of from about 25 amino acids to about 200 amino acids—e.g., from about 25 amino acids to about 50 amino acids, from about 50 amino acids to about 60 amino acids, from about 60 amino acids about 75 amino acids, from about 75 amino acids to about 80 amino acids, from about 80 amino acids to about 90 amino acids, from about 90 amino acids to about 100 amino acids, from about 100 amino acids to about 125 amino acids, from about 125 amino acids to about 150 amino acids, from about 150 amino acids to about 175 amino acids, or from about 175 amino acids to about 200 amino acids.

In some embodiments, the PBE does not naturally occur in the host cell so that only the engineered protein-protein interactions occur.

In some embodiments, two adjacent PBEs are separated by a linker. Suitable linkers include peptides of between about 6 and about 40 amino acids in length, e.g., from about 6 amino acids to about 8 amino acids, from about 8 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, or from about 35 amino acids to about 40 amino acids in length. In some embodiments, a peptide linker has a degree of flexibility. The linking peptides can have virtually any amino acid sequence, bearing in mind that linkers will have a sequence that results in a generally flexible peptide. Small amino acids, such as glycine and alanine, are of use in creating a flexible peptide. The creation of such sequences is routine to those of skill in the art. A variety of different linkers are commercially available and are considered suitable for use according to the present invention.

Amino acid sequences rich in alanine and proline residues are known to impart flexibility to multi-domain protein structures. For example, such sequences link the domains of the so-called E2 components of the 2-oxo acid dehydrogenase complexes, such as pyruvate dehydrogenase complex and 2-oxo glutarate dehydrogenase complex. Alanine-proline rich regions are also found in myosin light chains. Suitable linkers include peptides having multiple serine residues. Suitable linkers include peptides having multiple glycine residues. In some embodiments, a suitable linker includes peptides having multiple glycine and multiple serine residues, where exemplary linkers include, e.g., GSGSGSGGS (SEQ ID NO:2). Exemplary linkers have a combination of glycine, alanine, proline and methionine residues, such as AAAGGM (SEQ ID NO:3); AAAGGMPPAAAGGM (SEQ ID NO:4); AAAGGM (SEQ ID NO:5); and PPAAAGGMM (SEQ ID NO:6). However, any flexible linker generally between about 6 and about 40 amino acids in length may be used. Linkers may have virtually any sequence that results in a generally flexible peptide, including alanine-proline rich sequences of the type exemplified above.

A PBE binds a corresponding HP in a chimeric biosynthetic pathway enzyme via protein-protein interaction. Examples of such PBEs include, but are not limited to, a src homology 2 (SH2) domain; a phosphotyrosine binding (PTB) domain; a src homology 3 (SH3) domain; a GTPase Binding Domain (GBD); a leucine zipper domain; a forkhead associated (FHA) domain; a WW domain; a 14-3-3 domain; a death domain; a caspase recruitment domain (CARD); a bromodomain; a chromatin organization modifier; a shadow chromo domain; an F-box domain; a HECT domain; a RING finger domain; a sterile alpha motif (SAM) domain; a glycine-tyrosine-phenylalanine (GYF) domain; a soluble NSF attachment protein (SNAP) domain; a VHS domain; an ANK repeat; an armadillo repeat; a WD40 repeat; an MH2 domain; a calponin homology domain; a Dbl homology domain; a gelsolin homology domain; a phox and Bem1 (PB1) domain; a SOCS box; an RGS domain; a Toll/IL-1 receptor domain; a tetratricopeptide repeat; a TRAF domain; a Bcl-2 homology domain; a PSD95/DlgA/Zo-1 (PDZ) domain; a coiled-coil domain; a bZIP domain; and the like.

SH3

Suitable PBE include SH3 domains. SH3 domains include Class I SH3 domains; Class II SH3 domains; and unconventional SH3 domains. Amino acid sequences of SH3 domains are known in the art. See, for example, amino acids 136-189 of the amino acid sequence provided in GenBank Accession No. NP_058431 (*Homo sapiens* Crk protein); amino acids 136-189 of the amino acid sequence provided in GenBank Accession No. AAH31149 (*Mus musculus* Crk protein); and amino acids 4-77 of the amino acid sequence provided in GenBank Accession No. P27986 (*Homo sapiens* p85 subunit of phosphatidylinositol 3-kinase).

In some embodiments, an SH3 domain is a Class I SH3 domain and comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, from about 50 amino acids to about 60 amino acids, from about 60 amino acids to about 70 amino acids, or from about 70 amino acids to about 74 amino acids of the amino acid sequence: egyqyra lydykkeree didlhlgdil tvnkgslval gfsdgqearp eeigwlngyn ettgergdfp gtyveyi (SEQ ID NO:7).

In some embodiments, an SH3 domain is a Class II SH3 domain and comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, or from about 50 amino acids to about 54 amino acids of the amino acid sequence: yvralfdfngndeedlpfkkgdilrirdkpeeqwwnaedsegkrgmipvpyvek (SEQ ID NO:1). As one non-limiting example, an SH3 domain comprises the amino acid sequence: MAEYVRALFDFNGNDEEDLPFKKGDILRIRDKPEEQWWNAEDSEGKRGMIPVPYVEKY (SEQ ID NO:8).

An SH3 domain binds proline-rich peptides that form a left-handed poly-proline type II helix, where such peptides comprise the minimal consensus sequence Pro-X-X-Pro. In some embodiments, each Pro is preceded by an aliphatic residue. Exemplary, non-limiting examples of amino acid sequences of peptides comprising SH3 domain ligands include: RPLPVAP (SEQ ID NO:9; bound by a Class I SH3 domain); and PPPALPPKKR (SEQ ID NO:10; bound by a Class II SH3 domain).

PDZ

Suitable PBE include PDZ domains. Amino acid sequences of PDZ domains are known in the art. See, for example, amino acids 108-191, amino acids 201-287, and amino acids 354-434 of the amino acid sequence provided in Gen Bank Accession No. AAC52113 (*Homo sapiens* postsynaptic density protein 95); and amino acids 80-161 of the amino acid sequence provided in GenBank Accession No. NP_033254 (*Mus musculus* syntrophin).

In some embodiments, a suitable PDZ domain comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, from about 50 amino acids to about 60 amino acids, from about 60 amino acids to about 70 amino acids, from about 70 amino acids to about 80 amino acids, or from about 80 amino acids to about 84 amino acids of the amino acid sequence: eit lergnsglgf siaggtdnph igddpsifit kiipggaaaq dgrlrvndsi lfvnevdvre vthsaavealkeagsivrly v (SEQ ID NO11).

In some embodiments, a suitable PDZ domain comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, from about 50 amino acids to about 60 amino acids, from about 60 amino acids to about 70 amino acids, from about 70 amino acids to about 80 amino acids, or from about 80 amino acids to about 87 amino acids of the amino acid sequence: vmeiklikgp kglgfsiagg vgnqhipgdn siyvtkiieggaahkdgrlq igdkilavns vgledvmhed avaalkntyd vvylkva (SEQ ID NO:12).

In some embodiments, a suitable PDZ domain comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, from about 50 amino acids to about 60 amino acids, from about 60 amino acids to about 70 amino acids, or from about 70 amino acids to about 80 amino acids, of the amino acid sequence: rivih rgstglgfni vggedgegif isfilaggpa dlsgelrkgd qilsvngvdl rnasheqaaialknagqtvt iiaq (SEQ ID NO:13).

In some embodiments, a suitable PDZ domain comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, from about 50 amino acids to about 60 amino acids, from about 60 amino acids to about 70 amino acids, from about 70 amino acids to about 75 amino acids, or from about 75 amino acids to about 82 amino acids, of the amino acid sequence: r rvtvrkadag glgisikggr enkmpilisk ifkglaadqt ealfvgdail svngedlssa thdeavqalk ktgkevvlev k (SEQ ID NO:14). For example, a PDZ domain can comprise the amino acid sequence MLQRRRVTVRKADAGGLGISIKGGRENKMPILISKIFKGLAADQTEALFVGDAILSVNGEDLSSATHDEAVQALKKTGKEVVLEVKYMKEVSPYFKGS (SEQ ID NO:15).

GBD

Suitable PBE include GTPase-binding domains (GBD), also referred to in the art as CRIB (Cdc42/Rac-interactive binding) motifs. In some embodiments, a GBD binds a Cdc42p-like and/or a Rho-like small GTPase. Amino acid sequences of GBD are known in the art. See, e.g., amino acids 198-240 of the amino acid sequence provided in GenBank Accession No. NP_001103835 (*Rattus norvegicus* Wiskott-Aldrich syndrome-like protein (WASP)); amino acids 69-112 of the amino acid sequence provided in GenBank Accession No. Q13177 (*Homo sapiens* PAK-2); and amino acids 70-105 of the amino acid sequence provided in GenBank Accession No. P35465 (*Rattus norvegicus* PAK-1). See also the amino acid sequences PAK (75-111), ACK (504-549), and WASP (232-274), presented in FIG. 3A of Garrard et al. (2003) *EMBO J.* 22:1125. See also the amino acid sequences ACK (505-531), WASP (236-258), PAK1 (70-94), PAK2 (71-91), PAK-4 (6-30), presented in FIG. 1A of Bishop and Hall (2000) *Biochem. J.* 348:241.

In some embodiments, a suitable GBD comprises an amino acid sequence having at least about 75%, at least about 80%, at least about 85%, at least about 90%, at least about 95%, at least about 98%, at least about 99%, or 100%, amino acid sequence identity over a contiguous stretch of from about 20 amino acids to about 25 amino acids, from about 25 amino acids to about 30 amino acids, from about 30 amino acids to about 35 amino acids, from about 35 amino acids to about 40 amino acids, or from about 40 amino acids to about 43 amino acids, of the amino acid sequence: adi gtpsnfqhig hvgwdpntgf dlnnldpelk nlfdmcgise (SEQ ID NO:16).

In some embodiments, a suitable GBD comprises an amino acid sequence having at least about 75%, at least about 80%, at least about 85%, at least about 90%, at least about 95%, at least about 98%, at least about 99%, or 100%, amino acid sequence identity over a contiguous stretch of from about 20 amino acids to about 25 amino acids, from about 25 amino acids to about 30 amino acids, from about 30 amino acids to about 35 amino acids, from about 35 amino acids to about 40 amino acids, or from about 40 amino acids to about 42 amino acids, of the amino acid sequence: kerpeislpsdfehtihvgfdavtgeftgmpeqwar (SEQ ID NO:17).

In some embodiments, a suitable GBD comprises an amino acid sequence having at least about 75%, at least about 80%, at least about 85%, at least about 90%, at least about 95%, at least about 98%, at least about 99%, or 100%, amino acid sequence identity over a contiguous stretch of from about 45 amino acids to about 50 amino acids, from about 50 amino acids to about 55 amino acids, from about 55 amino acids to about 60 amino acids, from about 60 amino acids to about 65 amino acids, from about 65 amino acids to about 70 amino acids, from about 70 amino acids to about 75 amino acids, or from about 75 amino acids to about 80 amino acids, of the amino acid sequence: MTKADIGTPSNFQHIGHVGWDPNTGFDLNNLDPELKNLFDMCGISEAQLKDRETSKVIYDFIEKAVKNELRRQAP (SEQ ID NO:18).

Leucine Zipper Peptides

Suitable PBE include leucine zipper peptides. In some embodiments, leucine zipper peptides are peptides that interact via a coiled-coil domain. Amino acid sequences of leucine zipper domains are known in the art. Leucine zipper peptides include an EE12RR345L leucine zipper peptide; an RR12EE354L leucine zipper peptide; and the like.

An example of an amino acid sequence of a leucine zipper peptide is an EE12RR345L leucine zipper of the amino acid sequence: LEIEAAFLERENTALETRVAELRQRVQRLRNRVSQYRTRYGPLGGGK (SEQ ID NO:19).

In some embodiments, a leucine zipper peptide comprises an amino acid sequence having at least about 75%, at least about 80%, at least about 85%, at least about 90%, at least about 95%, at least about 98%, at least about 99%, or 100%, amino acid sequence identity over a contiguous stretch of from about 30 amino acids to about 35 amino acids, from about 35 amino acids to about 40 amino acids, or from about 40 amino acids to about 47 amino acids, of the amino acid sequence: LEIEAAFLERENTALETRVAELRQRVQRLRNRVSQYRTRYGPLGGGK (SEQ ID NO:20). Such a leucine zipper peptide can serve as a PBE or as an HP.

Another non-limiting example of an amino acid sequence of a leucine zipper peptide is an RR12EE345L leucine zipper peptide of the amino acid sequence: LEIRAAFLRQRNTALRTEVAELEQEVQRLENEVSQYETRYGPLGGGK (SEQ ID NO:21).

An EE12RR345L leucine zipper peptide as described above and an RR12EE345L leucine zipper peptide as described above bind to one another. In some embodiments, the EE12RR345L leucine zipper peptide is the PBE and the RR12EE345L leucine zipper peptide is the HP. In other embodiments, the RR12EE345L leucine zipper peptide is the PBE and the EE12RR345L leucine zipper peptide is the HP.

Exemplary Scaffolds

The following are exemplary, non-limiting examples of a subject scaffold.

In some embodiments, the biosynthetic pathway is a mevalonate pathway comprising two or more enzymes that produce an isoprenoid or an isoprenoid precursor. In some embodiments, the isoprenoid precursor is mevalonate. In some embodiments, the scaffold polypeptide is of the formula: $(X_1)_{n1}(Y_1)(X_2)_{n2}(Y_2)(X_3)_{n3}$, wherein the ratio of n2 to n3 provides for increased production of the product or product precursor.

In another embodiment, the scaffold polypeptide is of the formula: $(X_1)_{n1}(Y_1)(X_2)_{n2}(Y_2)(X_3)_{n3}(Y_3)$, wherein $X_1$ is a PBE that binds a corresponding HP in a chimeric acetoacetyl CoA thiolase, $X_2$ is a PBE that binds a corresponding HP in a chimeric HMGS, and $X_3$ is a PBE that binds a corresponding HP in a chimeric HMGR. In some embodiments, $X_1$ is a GBD, and n1=1; $X_2$ is an SH3 domain, and n2=1, 2, or 4; and $X_3$ is a PDZ domain, and n3=1, 2, or 4; where the chimeric acetoacetyl CoA thiolase comprises an HP that binds the $X_1$ GBD, where the chimeric HMGS comprises an HP that binds the $X_2$ SH3 domain, and where the chimeric HMGR comprises an HP that binds the $X_3$ PDZ domain.

Heterologous Peptides

A heterologous peptide (HP) present in a chimeric biosynthetic pathway enzyme binds a corresponding PBE in the scaffold polypeptide. For convenience, a biosynthetic pathway enzyme that comprises an HP is referred to herein as a "chimeric biosynthetic pathway enzyme." A chimeric biosynthetic pathway enzyme bind to a PBE in the scaffold polypeptide with a Kd of from about 0.01 μM to about $10^3$ μM, e.g., from about 0.01 μM to about 0.05 μM, from about 0.05 μM to about 0.1 μM, from about 0.1 μM to about 0.5 μM, from about 0.5 μM to about 1.0 μM, from about 1.0 μM to about 5 μM, from about 5 μM to about 10 μM, from about 10 μM to about 50 μM, from about 50 μM to about $10^2$ μM, from about $10^2$ μM to about $5\times10^2$ μM, or from about $5\times10^2$ μM to about $10^3$ μM. Stated another way, a given PBE binds a ligand HP with a Kd of from about 0.01 μM to about $10^3$ μM, e.g., from about 0.01 μM to about 0.05 μM, from about 0.05 μM to about 0.1 μM, from about 0.1 μM to about 0.5 μM, from about 0.5 μM to about 1.0 μM, from about 1.0 μM to about 5 μM, from about 5 μM to about 10 μM, from about 10 μM to about 50 μM, from about 50 μM to about $10^2$ μM, from about $10^2$ μM to about $5\times10^2$ μM, or from about $5\times10^2$ μM to about $10^3$ μM.

An HP has a length of from about 4 amino acids to about 50 amino acids, e.g., an HP has a length of 4 amino acids, 5 amino acids, 6 amino acids, from 7 amino acids to 10 amino acids, from 10 amino acids to 12 amino acids, from 12 amino acids to 15 amino acids, from 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids.

The HP can be linked to a biosynthetic pathway enzyme at the amino terminus of the enzyme, at the carboxyl terminus of the enzyme, or at an internal site within the enzyme. In some embodiments, a chimeric biosynthetic pathway enzyme comprises, in order from amino terminus to carboxyl terminus: a) an HP; and b) a biosynthetic pathway enzyme. In other embodiments, a chimeric biosynthetic pathway enzyme comprises, in order from amino terminus to carboxyl terminus: a) a biosynthetic pathway enzyme; and b) an HP. In other embodiments, a chimeric biosynthetic pathway enzyme comprises, in order from amino terminus to carboxyl terminus: a) a first portion of the biosynthetic pathway enzyme; b) an HP; and c) a second portion of the biosynthetic pathway enzyme. Where the HP is located at a site internal to the biosynthetic pathway enzyme, the HP does not substantially reduce the enzymatic activity of the biosynthetic pathway enzyme.

SH3 Domain Ligands

In some embodiments, an HP is an SH3 domain ligand. An SH3 domain binds proline-rich peptides that form a left-handed poly-proline type II helix, where such peptides comprise the minimal consensus sequence Pro-X-X-Pro. In some embodiments, each Pro is preceded by an aliphatic residue. Exemplary, non-limiting examples of amino acid sequences of peptides comprising SH3 domain ligands include: RPLPVAP (SEQ ID NO:9; bound by a Class I SH3 domain); PPPALPPKRRRPG (SEQ ID NO:22); and PPPALPPKKR (SEQ ID NO:10; bound by a Class II SH3 domain).

PDZ Domain Ligands

In some embodiments, an HP is a PDZ domain ligand. A PDZ domain binds to the C-terminal 4-5 residues of target proteins. In some embodiments, a consensus PDZ domain ligand comprises a hydrophobic residue, e.g., Val or Ile, at the carboxyl terminus. Exemplary, non-limiting examples of amino acid sequences of peptides comprising PDZ domain ligands include: IESDV (SEQ ID NO:23); VKESLV (SEQ ID NO:24); GVKESLV (SEQ ID NO:25); GVKQSLL (SEQ ID NO:26); GVKESGA (SEQ ID NO:27); YVKESLV (SEQ ID NO:28); and VETDV (SEQ ID NO:29).

GBD Ligands

In some embodiments, an HP is a GBD ligand. An exemplary, non-limiting GBD ligand comprises the amino acid sequence LVGALMHVMQKRSRAIHSSDEGEDQAGDEDED (SEQ ID NO:30).

Leucine Zipper Domain Ligands

In some embodiments, an HP is a leucine zipper domain ligand. Suitable HP include leucine zipper peptides. In some embodiments, leucine zipper peptides are peptides that interact via a coiled-coil domain. Amino acid sequences of leucine zipper domains are known in the art. Leucine zipper peptides include an EE12RR345L leucine zipper peptide; an RR12EE354L leucine zipper peptide; and the like.

An example of an amino acid sequence of a leucine zipper peptide is an EE12RR345L leucine zipper of the amino acid sequence: LEIEAAFLERENTALETRVAELRQRVQRLR NRVSQYRTRYGPLGGGK (SEQ ID NO:31).

Another non-limiting example of an amino acid sequence of a leucine zipper peptide is an RR12EE345L leucine zipper peptide of the amino acid sequence: LEIRAAFLRQRNTA-LRT EVAELEQEVQRLENEVSQYETRYGPLGGGK (SEQ ID NO:32).

An EE12RR345L leucine zipper peptide as described above and an RR12EE345L leucine zipper peptide as described above bind to one another. In some embodiments, the EE12RR345L leucine zipper peptide is the PBE and the RR12EE345L leucine zipper peptide is the HP. In other embodiments, the RR12EE345L leucine zipper peptide is the PBE and the EE12RR345L leucine zipper peptide is the HP.

Nucleic Acids

The present invention provides a nucleic acid comprising a nucleotide sequence encoding a scaffold polypeptide as described above. In some embodiments, a subject nucleic acid comprises a nucleotide sequence encoding a subject scaffold polypeptide. In some embodiments, the scaffold polypeptide-encoding nucleotide sequence is operably linked to a transcriptional control element. In some embodiments, a subject nucleic acid comprises: 1) a nucleotide sequence encoding a scaffold polypeptide; and 2) nucleotide sequences encoding two or more enzymes in a biosynthetic pathway, where the enzymes are chimeric biosynthetic pathway enzymes comprising a heterologous peptide that provides for binding to a binding element within the scaffold polypeptide. The biosynthetic pathway enzymes are chimeric biosynthetic pathway enzymes, e.g., chimeric biosynthetic pathway enzymes that comprise a heterologous peptide that is a ligand for a corresponding peptide binding element in the scaffold polypeptide.

In some embodiments, a nucleotide sequence encoding a scaffold polypeptide and the nucleotide sequences encoding two or more chimeric biosynthetic pathway enzymes are on the same nucleic acid. Where a nucleotide sequence encoding a scaffold polypeptide and the nucleotide sequences encoding two or more chimeric biosynthetic pathway enzymes are on the same nucleic acid, in some embodiments, the nucleotide sequences encoding two or more chimeric biosynthetic pathway enzymes are operably linked to a first transcriptional control element, and the nucleotide sequence encoding the scaffold polypeptide is operably linked to the first transcriptional control element. Where a nucleotide sequence encoding a scaffold polypeptide and the nucleotide sequences encoding two or more chimeric biosynthetic pathway enzymes are on the same nucleic acid, in some embodiments, the nucleotide sequences encoding two or more chimeric biosynthetic pathway enzymes are operably linked to a first transcriptional control element, and the nucleotide sequence encoding the scaffold polypeptide is operably linked to a second control element. In other embodiments, a nucleotide sequence encoding a scaffold polypeptide and the nucleotide sequences encoding two or more chimeric biosynthetic pathway enzymes are on separate nucleic acids.

Expression Constructs

In some embodiments, a subject nucleic acid comprising a nucleotide sequence encoding a subject scaffold polypeptide is present in an expression construct. Such an expression construct can, when introduced into a host cell, provide for production of the encoded scaffold polypeptide in the host cell. In some embodiments, a subject expression construct comprises a nucleotide sequence encoding a subject scaffold polypeptide. In some embodiments, a subject expression construct comprises: 1) a nucleotide sequence encoding a scaffold polypeptide; and 2) nucleotide sequences encoding two or more chimeric biosynthetic pathway enzymes. Expression constructs generally include one or more transcriptional control elements, and a selectable marker.

Transcriptional Control Elements

Non-limiting examples of suitable eukaryotic promoters include CMV immediate early, HSV thymidine kinase, early and late SV40, LTRs from retrovirus, and mouse metallothionein-I. In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, the promoter is an inducible promoter. In some embodiments, the promoter is a constitutive promoter. In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D. C.). Alternatively, vectors may be used which promote integration of foreign DNA sequences into the yeast chromosome.

In some embodiments, a promoter or other regulatory element(s) suitable for expression in a plant cell is used. Non-limiting examples of suitable constitutive promoters that are functional in a plant cell is the cauliflower mosaic virus 35S promoter, a tandem 35S promoter (Kay et al., *Science* 236: 1299 (1987)), a cauliflower mosaic virus 19S promoter, a nopaline synthase gene promoter (Singer et al., *Plant Mol. Biol.* 14:433 (1990); An, *Plant Physiol.* 81:86 (1986), an octopine synthase gene promoter, and a ubiquitin promoter. Suitable inducible promoters that are functional in a plant cell include, but are not limited to, a phenylalanine ammonialyase gene promoter, a chalcone synthase gene promoter, a pathogenesis-related protein gene promoter, a copper-inducible regulatory element (Mett et al., *Proc. Natl. Acad. Sci. USA* 90:4567-4571 (1993); Furst et al., Cell 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992); a nitrate-inducible promoter derived from the spinach nitrite reductase gene (Back et al., *Plant Mol. Biol.* 17:9 (1991)); a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)); a light-responsive regulatory element as described in U.S. Patent Publication No. 20040038400; a salicylic acid inducible regulatory elements (Uknes et al., *Plant Cell* 5:159-169 (1993); Bi et al., *Plant J.* 8:235-245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991).

Plant tissue-selective regulatory elements also can be included in a subject nucleic acid or a subject vector. Suitable tissue-selective regulatory elements, which can be used to ectopically express a nucleic acid in a single tissue or in a limited number of tissues, include, but are not limited to, a xylem-selective regulatory element, a tracheid-selective regulatory element, a fiber-selective regulatory element, a trichome-selective regulatory element (see, e.g., Wang et al. (2002) *J. Exp. Botany* 53:1891-1897), a glandular trichome-selective regulatory element, and the like.

Vectors that are suitable for use in plant cells are known in the art, and any such vector can be used to introduce a subject nucleic acid into a plant host cell. Suitable vectors include, e.g., a Ti plasmid of *Agrobacterium tumefaciens* or an Ri$_1$ plasmid of *A. rhizogenes*. The Ti or Ri$_1$ plasmid is transmitted to plant cells on infection by *Agrobacterium* and is stably integrated into the plant genome. J. Schell, *Science,* 237: 1176-83 (1987). Also suitable for use is a plant artificial chromosome, as described in, e.g., U.S. Pat. No. 6,900,012.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.,* 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction.* Macmillan, London, UK, Vol. 10, pp. 143-162); an SP6 promoter (see, e.g., Melton et al. (1984) *Nucl. Acids Res.* 12:7035-7056); and the like. Suitable strong promoters for use in prokaryotes such as *Escherichia coli* include, but are not limited to Trc, Tac, T5, T7, and P$_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) *Proc. Natl. Acad. Sci. U.S.A.* 80:21-25.)

Non-limiting examples of suitable constitutive promoters for use in prokaryotic host cells include a sigma70 promoter (for example, a consensus sigma70 promoter). Non-limiting examples of suitable inducible promoters for use in bacterial host cells include the pL of bacteriophage λ; Plac; Ptrp; Ptac (Ptrp-lac hybrid promoter); an isopropyl-beta-D44 thiogalactopyranoside (IPTG)-inducible promoter, for example, a lacZ promoter; a tetracycline inducible promoter; an arabinose inducible promoter, for example, PBAD (see, for example, Guzman et al. (1995) *J. Bacteriol.* 177:4121-4130); a xylose-inducible promoter, for example, Pxyl (see, for example, Kim et al. (1996) *Gene* 181:71-76); a GAL1 promoter; a tryptophan promoter; a lac promoter; an alcohol-inducible promoter, for example, a methanol-inducible promoter, an ethanol-inducible promoter; a raffinose-inducible promoter; a heat-inducible promoter, for example, heat inducible lambda PL promoter; a promoter controlled by a heat-sensitive repressor (for example, CI857-repressed lambda-based expression vectors; see, for example, Hoffmann et al. (1999) *FEMS* Microbiol Lett. 177(2):327-34); and the like.

Expression Vectors

Suitable expression vectors include any of a variety of expression vectors available in the art; and variant and derivatives of such vectors. Those of ordinary skill in the art are familiar with selecting appropriate expression vectors for a given application. Numerous suitable expression vectors are known to those of skill in the art, and many are commercially available. Suitable expression vectors for use in constructing the host cells include, but are not limited to, baculovirus vectors, bacteriophage vectors, plasmids, phagemids, cosmids, fosmids, bacterial artificial chromosomes, viral vectors (for example, viral vectors based on vaccinia virus, poliovirus, adenovirus, adeno-associated virus, SV40, herpes simplex virus, and the like), P1-based artificial chromosomes, yeast plasmids, yeast artificial chromosomes, and other vectors. A typical expression vector contains an origin of replication that ensures propagation of the vector, a nucleic acid sequence that encodes a desired enzyme, and one or more regulatory elements that control the synthesis of the desired enzyme.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, an expression vector can be constructed to yield a desired level of copy numbers of the vector. In some embodiments, an expression vector provides for at least 10, between 10 to 20, between 20-50, between 50 and 100, or more than 100 copies of the expression vector in the host cell. Low copy number plasmids generally provide fewer than about 20 plasmid copies per cell; medium copy number plasmids generally provide from about 20 plasmid copies per cell to about 50 plasmid copies per cell, or from about 20 plasmid copies per cell to about 80 plasmid copies per cell; and high copy number plasmids generally provide from about 80 plasmid copies per cell to about 200 plasmid copies per cell, or more than 200 plasmid copies per cell. In some embodiments, the expression vector is a low copy number vector.

Suitable low-copy (centromeric) expression vectors for yeast include, but are not limited to, pRS415 and pRS416 (Sikorski & Hieter (1989) *Genetics* 122:19-27). In some embodiments, the enzyme-encoding sequences are present on one or more medium copy number plasmids. Medium copy number plasmids generally provide from about 20 plasmid copies per cell to about 50 plasmid copies per cell, or from about 20 plasmid copies per cell to about 80 plasmid copies per cell. Medium copy number plasmids for use in yeast include, e.g., Yep24. In some embodiments, the enzyme-encoding sequences are present on one or more high copy number plasmids. High copy number plasmids generally provide from about 30 plasmid copies per cell to about 200 plasmid copies per cell, or more. Suitable high-copy 2 micron expression vectors in yeast include, but are not limited to, pRS420 series vectors, e.g., pRS425 and pRS426 (Christianson et al. (1992) *Gene* 110:119-122).

Exemplary low copy expression vectors for use in prokaryotes such as *Escherichia coli* include, but are not limited to, pACYC184, pBeloBac11, pBR332, pBAD33, pBBR1MCS and its derivatives, pSC101, SuperCos (cosmid), and pWE15 (cosmid). Suitable medium copy expression vectors for use in prokaryotes such as *Escherichia coli* include, but are not limited to pTrc99A, pBAD24, and vectors containing a ColE1 origin of replication and its derivatives. Suitable high copy number expression vectors for use in prokaryotes such as *Escherichia coli* include, but are not limited to, pUC, pBluescript, pGEM, and pTZ vectors.

The expression vector can also contain one or more selectable marker genes that, upon expression, confer one or more phenotypic traits useful for selecting or otherwise identifying host cells that carry the expression vector. Non-limiting examples of suitable selectable markers for prokaryotic cells include resistance to an antibiotic such as tetracycline, ampicillin, chloramphenicol, carbenicillin, or kanamycin.

In some embodiments, instead of antibiotic resistance as a selectable marker for the expression vector, a subject method will employ host cells that do not require the use of an antibiotic resistance conferring selectable marker to ensure plasmid (expression vector) maintenance. In these embodiments, the expression vector contains a plasmid maintenance system such as the 60-kb IncP (RK2) plasmid, optionally together with the RK2 plasmid replication and/or segregation system, to effect plasmid retention in the absence of antibiotic selection (see, for example, Sia et al. (1995) J. Bacteriol. 177: 2789-97; Pansegrau et al. (1994) J. Mol. Biol. 239:623-63). A suitable plasmid maintenance system for this purpose is encoded by the parDE operon of RK2, which codes for a stable toxin and an unstable antitoxin. The antitoxin can inhibit the lethal action of the toxin by direct protein-protein interaction. Cells that lose the expression vector that harbors the parDE operon are quickly deprived of the unstable antitoxin, resulting in the stable toxin then causing cell death. The RK2 plasmid replication system is encoded by the trfA gene, which codes for a DNA replication protein. The RK2 plasmid segregation system is encoded by the parCBA operon, which codes for proteins that function to resolve plasmid multimers that may arise from DNA replication.

Biosynthetic Pathway Enzymes

As noted above, in some embodiments, a subject nucleic acid comprises: 1) a nucleotide sequence encoding a scaffold polypeptide; and 2) nucleotide sequences encoding two or more enzymes in a biosynthetic pathway, where the enzymes are chimeric biosynthetic pathway enzymes comprising: a) a biosynthetic pathway enzyme; and b) a heterologous peptide that provides for binding to a binding element within the scaffold polypeptide. Suitable biosynthetic pathway enzymes include, but are not limited to, enzymes that form an isoprenoid biosynthetic pathway; enzymes that form an alkaloid biosynthetic pathway; enzymes that form a phenylpropanoid biosynthetic pathway; and enzymes that form a polyketide biosynthetic pathway.

Alkaloid biosynthetic pathway enzymes are known in the art. See, e.g., ((2004) *TRENDS Plant Sci.* 9:116; Pauli and Kutchan ((1998) *Plant J.* 13:793-801; Collu et al. ((2001) *FEBS Lett.* 508:215-220; Schroder et al. ((1999) *FEBS Lett.* 458:97-102. Phenylpropanoid biosynthetic pathway enzymes are known in the art. See, e.g., Mizutani et al. ((1997) *Plant Physiol.* 113:755-763; and Gang et al. ((2002) *Plant Physiol.* 130:1536-1544. Polyketide biosynthetic pathway enzymes are known in the art. See e.g., Ikeda et al. ((1999) *Proc. Natl. Acad. Sci. USA* 96:9509-9514; and Ward et al. ((2004) *Antimicrob. Agents Chemother.* 48:4703-4712. Isoprenoid biosynthetic pathway enzymes are described in more detail below.

In some embodiments, the nucleotide sequence encoding a biosynthetic pathway enzyme encodes a biosynthetic pathway enzyme that has from about 50% to about 55%, from about 55% to about 60%, from about 60% to about 65%, from about 65% to about 70%, from about 70% to about 75%, from about 75% to about 80%, from about 80% to about 85%, from about 85% to about 90%, or from about 90% to about 95% amino acid sequence identity to the amino acid sequence of a naturally-occurring biosynthetic pathway enzyme. In some embodiments, the encoded biosynthetic pathway enzyme comprises one or more modifications relative to a wild-type biosynthetic pathway enzyme. For example, in some embodiments, the encoded biosynthetic pathway enzyme will have a non-native (non-wild-type, or non-naturally occurring, or variant) amino acid sequence. In some embodiments, the encoded biosynthetic pathway enzyme will have one or more amino acid sequence modifications (deletions, additions, insertions, substitutions) that increase the level of activity of the biosynthetic pathway enzyme.

Isoprenoid Biosynthetic Pathway Enzymes

In some embodiments, a subject nucleic acid comprises: 1) a nucleotide sequence encoding a scaffold polypeptide; and 2) nucleotide sequences encoding two or more enzymes in an isoprenoid biosynthetic pathway, where the enzymes are chimeric biosynthetic pathway enzymes comprising: a) an isoprenoid biosynthetic pathway enzyme; and b) a heterologous peptide that provides for binding to a binding element within the scaffold polypeptide. The two or more isoprenoid biosynthetic pathway enzymes provide for production of an isoprenoid or an isoprenoid precursor (e.g., isopentenyl pyrophosphate (IPP), mevalonate, etc). In some embodiments, the two or more isoprenoid biosynthetic pathway enzymes comprise mevalonate pathway enzymes. In other embodiments, the two or more isoprenoid biosynthetic pathway enzymes comprise DXP pathway enzymes.

In some embodiments, nucleotide sequences encoding two or more enzymes in an isoprenoid biosynthetic pathway comprise nucleotide sequences encoding two, three, four, five, six, seven, eight, or more of: an acetoacetyl-CoA thiolase, a hydroxymethyl glutaryl-CoA synthase (HMGS), a hydroxymethyl glutaryl-CoA reductase (HMGR), a mevalonate kinase (MK), a phosphomevalonate kinase (PMK), and a mevalonate pyrophosphate decarboxylase (MPD), an isopentenyl pyrophosphate (IPP) isomerase, a prenyl transferase, and a terpene synthase.

Nucleotide sequences encoding mevalonate (MEV) pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (AB015627; *Streptomyces* sp. KO-3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315 . . . 713670; *Saccharomyces cerevisiae*);

MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), and (AF082326; *Haematococcus pluvialis*).

In some embodiments, the HMGR coding region encodes a truncated form of HMGR ("tHMGR") that lacks the transmembrane domain of wild-type HMGR. The transmembrane domain of HMGR contains the regulatory portions of the enzyme and has no catalytic activity.

In some embodiments, a nucleic acid comprises a nucleotide sequence encoding a MEV pathway enzyme that has at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% amino acid sequence identity to a known or naturally-occurring MEV pathway enzyme.

The coding sequence of any known MEV pathway enzyme may be altered in various ways known in the art to generate targeted changes in the amino acid sequence of the encoded enzyme. The amino acid sequence of a variant MEV pathway enzyme will in some embodiments be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Exemplary nucleotide sequences encoding MEV pathway enzymes include: 1) nucleotide sequences encoding acetoacetyl-CoA thiolase, HMGS, HMGR, MK, PMK, and MPD (e.g., SEQ ID NO:7 of U.S. Pat. No. 7,192,751); 2) nucleotide sequences encoding the "bottom half" of a mevalonate pathway (e.g., MK, PMK, and MPD; e.g., SEQ ID NO:9 of U.S. Pat. No. 7,192,751); 3) nucleotide sequences encoding MK, PMK, MPD, and isopententyl pyrophosphate isomerase (idi) (e.g., SEQ ID NO:12 of U.S. Pat. No. 7,192,751); and 4) nucleotide sequences encoding MK, PMK, MPD, idi, and an FPP synthase (e.g., SEQ ID NO:13 of U.S. Pat. No. 7,192,751; e.g., SEQ ID NO:4 of U.S. Pat. No. 7,183,089).

DXP Pathway Enzymes

In some embodiments, a subject nucleic acid comprises nucleotide sequences encoding one, two, three, four, five, or six enzymes in the DXP pathway, e.g., the nucleotide sequences encode one or more of 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), and 1-hydroxy-2-methyl-2-(E)-butenyl 4-diphosphate synthase (IspG).

Nucleotide sequences encoding DXP pathway enzymes are known in the art, and can be used in a subject nucleic acid. Variants of any known nucleotide sequence encoding a DXP pathway enzyme can be used, where the encoded enzyme retains enzymatic activity. Variants of any known nucleotide sequence encoding a DXP pathway enzyme selected from 1-deoxy-D-xylulose-5-phosphate synthase (dxs); 1-deoxy-D-xylulose-5-phosphate reductoisomerase (IspC; dxr), 4-diphosphocytidyl-2-C-methyl-D-erythritol synthase (IspD; YbgP), 4-diphosphocytidyl-2-C-methyl-D-erythritol kinase (IspE; YchB), 2C-methyl-D-erythritol 2,4-cyclodiphosphate synthase (IspF; YbgB), 1-hydroxy-2-methyl-2-(E)-butenyl 4-diphosphate synthase (IspG), and isopentenyl diphosphate isomerase can be used, where a variant differs in nucleotide sequence by one or more nucleotides from a reference sequence (e.g., a known sequence); and where a variant nucleotide sequence includes one or more nucleotide substitutions, insertions, truncations, or deletions, compared to a reference sequence, e.g., compared to a known sequence.

The coding sequence of any known DXP pathway enzyme may be altered in various ways known in the art to generate targeted changes in the amino acid sequence of the encoded enzyme. The amino acid of a variant DXP pathway enzyme will in some embodiments be substantially similar to the amino acid sequence of any known DXP pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Nucleotide sequences encoding 1-deoxy-D-xylulose-5-phosphate synthase (dxs) are known in the art. See, e.g., GenBank Accession No. DQ768815 (*Yersinia pestis* dxs); GenBank Accession No. AF143812 (*Lycopersicon esculentum* dxs); GenBank Accession No. Y18874 (*Synechococcus* PCC6301 dxs); GenBank Accession No. AF035440; *E. coli* dxs); GenBank Accession No. AF282878 (*Pseudomonas aeruginosa* dxs); GenBank Accession No. NM_121176 (*Arabidopsis thaliana* dxs); and GenBank Accession No. AB026631 (*Streptomyces* sp. CL190 dxs). Swissprot accession No. O78328 (*Capsicum annum*). See also FIG. 5 of U.S. Patent Publication No. 2003/0219798 for nucleotide sequences encoding dxs.

Nucleotide sequences encoding 1-deoxy-D-xylulose-5-phosphate reductoisomerase (IspC; dxr) are known in the art. See, e.g., GenBank Accession No. AF282879 (*Pseudomonas aeruginosa* dxr); GenBank Accession No. AY081453 (*Arabidopsis thaliana* dxr); and GenBank Accession No. AJ297566 (*Zea mays* dxr). See also FIG. 31 of U.S. Patent Publication No. 2003/0219798 for nucleotide sequences encoding dxr.

Nucleotide sequences encoding 4-diphosphocytidyl-2-C-methyl-D-erythritol synthase (IspD; YbgP) are known in the art. See, e.g., GenBank Accession No. AF230737 (*Arabidopsis thaliana*); GenBank Accession No. CP000034.1 (nucleotides 2725605-2724895; *Shigella dysenteriae*); and GenBank Accession No. CP000036.1 (nucleotides 2780789 to 2781448; *Shigella boydii*). See also SEQ ID NO:5 of U.S. Pat. No. 6,660,507 (*Methylomonas* IspD).

Nucleotide sequences encoding 4-diphosphocytidyl-2-C-methyl-D-erythritol (IspE; YchB) kinase are known in the art. See, e.g., GenBank Accession No. CP000036.1 (nucleotides 1839782-1840633; *Shigella boydii*); GenBank Accession No. AF288615 (*Arabidopsis thaliana*) and GenBank Accession No. CP000266.1 (nucleotides 1272480-1271629; *Shigella flexneri*). See also, SEQ ID NO:7 of U.S. Pat. No. 6,660,507 (*Methylomonas* 16a IspE).

Nucleotide sequences encoding 2C-methyl-D-erythritol 2,4-cyclodiphosphate synthase (IspF; YbgB) are known in the art. See, e.g., GenBank Accession No. AE017220.1 (nucleotides 3025667-3025216; *Salmonella enterica* IspF); Gen- Bank Accession No. NM_105070 (*Arabidopsis thaliana*); GenBank Accession No. AE014073.1 (nucleotides 2838621-283841; *Shigella flexneri*).

Nucleotide sequences encoding 1-hydroxy-2-methyl-2-(E)-butenyl 4-diphosphate synthase (IspG; GcpE) are known in the art. See, e.g., GenBank Accession No. CP000034.1 (nucleotides 2505082 to 2503964; *Shigella dysenteriae* IspG); GenBank Accession No. NM_180902 (*Arabidopsis thaliana*); GenBank Accession No. AE008814.1 (nucleotides 15609-14491; *Salmonella typhimurium* IsgG); GenBank Accession No. AE014613.1 (nucleotides 383225-384343; *Salmonella enterica* GcpE); GenBank Accession No. AE017220.1 (nucleotides 2678054-2676936; *Salmonella enterica* GcpE; and GenBank Accession No. BX95085.1 (nucleotides 3604460-3603539; *Erwinia carotova* GcpE).

IspH genes are known in the art. See, e.g., GenBank Accession No. AY168881 (*Arabidopsis thaliana*).

Nucleotide sequences encoding IPP isomerase are known in the art. See, e.g., (J05090; *Saccharomyces cerevisiae*); Wang and Ohnuma (2000) *Biochim. Biophys. Acta* 1529:33-48; GenBank Accession No. NM_121649 (*Arabidopsis thaliana*); U.S. Pat. No. 6,645,747; SEQ ID NO:1 of WO 02/095011; and SEQ ID NO:50 of WO 02/083720.

Prenyl Transferases

In some embodiments, a genetically modified host cell is genetically modified to include a nucleic acid comprising a nucleotide sequence encoding a scaffold polypeptide; and in some embodiments is also genetically modified to include one or more nucleic acids comprising a nucleotide sequence(s) encoding one or more mevalonate pathway enzymes, as described above; and a nucleic acid comprising a nucleotide sequence that encodes a prenyl transferase.

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 2 isoprene units to about 6000 isoprene units or more, e.g., 2 isoprene units (Geranyl Pyrophosphate synthase), 3 isoprene units (Farnesyl pyrophosphate synthase), 4 isoprene units (geranylgeranyl pyrophosphate synthase), 5 isoprene units, 6 isoprene units (hexadecylpyrophosphate synthase), 7 isoprene units, 8 isoprene units (phytoene synthase, octaprenyl pyrophosphate synthase), 9 isoprene units (nonaprenyl pyrophosphate synthase, 10 isoprene units (decaprenyl pyrophosphate synthase), from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50 isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of a numerous prenyl transferases from a variety of species are known, and can be used or modified for use in generating a genetically modified host cell. Nucleotide sequences encoding prenyl transferases are known in the art. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*); Wang and Ohnuma (2000) *Biochim. Biophys. Acta* 1529:33-48; U.S. Pat. No. 6,645,747; *Arabidopsis thaliana* farnesyl pyrophosphate synthetase 2 (FPS2)/FPP synthetase 2/farnesyl diphosphate synthase 2 (At4g17190) mRNA (GenBank Accession No. NM_202836); *Ginkgo biloba* geranylgeranyl diphosphate synthase (ggpps) mRNA (GenBank Accession No. AY371321); *Arabidopsis thaliana* geranylgeranyl pyrophosphate synthase (GGPS1)/GGPP synthetase/farnesyltranstransferase (At4g36810) mRNA (GenBank Accession No. NM_119845); *Synechococcus elongatus* gene for farnesyl, geranylgeranyl, geranylfarnesyl, hexaprenyl, heptaprenyl diphosphate synthase (SelF-HepPS) (GenBank Accession No. AB016095); etc.

Terpene Synthases

In some embodiments, a genetically modified host cell is further genetically modified to include a nucleic acid comprising a nucleotide sequence encoding a terpene synthase. In some embodiments, the terpene synthase is one that modifies FPP to generate a sesquiterpene. In other embodiments, the terpene synthase is one that modifies GPP to generate a monoterpene. In other embodiments, the terpene synthase is one that modifies GGPP to generate a diterpene. The terpene synthase acts on a polyprenyl diphosphate substrate, modifying the polyprenyl diphosphate substrate by cyclizing, rearranging, or coupling the substrate, yielding an isoprenoid precursor (e.g., limonene, amorphadiene, taxadiene, etc.), which isoprenoid precursor is the substrate for an isoprenoid precursor-modifying enzyme(s). By action of the terpene synthase on a polyprenyl diphosphate substrate, the substrate for an isoprenoid-precursor-modifying enzyme is produced.

Nucleotide sequences encoding terpene synthases are known in the art, and any known terpene synthase-encoding nucleotide sequence can be used to genetically modify a host cell. For example, the following terpene synthase-encoding nucleotide sequences, followed by their GenBank accession numbers and the organisms in which they were identified, are known and can be used: (−)-germacrene D synthase mRNA (AY438099; *Populus balsamifera* subsp. *trichocarpa×Populus deltoids*); E,E-alpha-farnesene synthase mRNA (AY640154; *Cucumis sativus*); 1,8-cineole synthase mRNA (AY691947; *Arabidopsis thaliana*); terpene synthase 5 (TPS5) mRNA (AY518314; *Zea mays*); terpene synthase 4 (TPS4) mRNA (AY518312; *Zea mays*); myrcene/ocimene synthase (TPS10) (At2g24210) mRNA (NM_127982; *Arabidopsis thaliana*); geraniol synthase (GES) mRNA (AY362553; *Ocimum basilicum*); pinene synthase mRNA (AY237645; *Picea sitchensis*); myrcene synthase 1e20 mRNA (AY195609; *Antirrhinum majus*); (E)-β-ocimene synthase (0e23) mRNA (AY195607; *Antirrhinum majus*); E-β-ocimene synthase mRNA (AY151086; *Antirrhinum majus*); terpene synthase mRNA (AF497-492; *Arabidopsis thaliana*); (−)-camphene synthase (AG6.5) mRNA (U87910; *Abies grandis*); (−)-4S-limonene synthase gene (e.g., genomic sequence) (AF326518; *Abies grandis*); delta-selinene synthase gene (AF326513; *Abies grandis*); amorpha-4,11-diene synthase mRNA (AJ251751; *Artemisia annua*); E-α-bisabolene synthase mRNA (AF006195; *Abies grandis*); gamma-humulene synthase mRNA (U92267; *Abies grandis*); δ-selinene synthase mRNA (U92266; *Abies grandis*); pinene synthase (AG3.18) mRNA (U87909; *Abies grandis*); myrcene synthase (AG2.2) mRNA (U87908; *Abies grandis*); etc.

Codon Usage

In some embodiments, a nucleotide sequence is modified such that the nucleotide sequence reflects the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another example, in some embodiments, the nucleotide sequence will be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292.

Genetically Modified Host Cells

The present invention provides genetically modified host cells, wherein host cells are genetically modified a subject nucleic acid comprising a nucleotide sequence encoding a scaffold polypeptide as described above. In some embodiments, a subject genetically modified host cell comprises a nucleic acid comprises a nucleotide sequence encoding a subject scaffold polypeptide. In some embodiments, the nucleic acid is an expression construct, and the encoded scaffold polypeptide is produced in the genetically modified host cell.

In some embodiments, a subject genetically modified host cell comprises one or more nucleic acids comprising: 1) a nucleotide sequence encoding a scaffold polypeptide; and 2) nucleotide sequences encoding one, two, or more enzymes in a biosynthetic pathway, where the enzymes are chimeric biosynthetic pathway enzymes comprising a heterologous peptide that provides for binding to a binding element within the scaffold polypeptide. The biosynthetic pathway enzymes are chimeric biosynthetic pathway enzymes, e.g., chimeric biosynthetic pathway enzymes that comprise a heterologous peptide that is a ligand for a corresponding peptide binding element in the scaffold polypeptide. In some embodiments, the one or more nucleic acids are expression constructs that provide for production of the encoded scaffold polypeptide and the two or more chimeric biosynthetic pathway enzymes in the genetically modified host cell.

To generate a genetically modified host cell, one or more heterologous nucleic acids is introduced stably or transiently into a parent host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like. Stable transformation can also be effected (e.g., selected for) using a nutritional marker gene that confers prototrophy for an essential amino acid such as URA3, HIS3, LEU2, MET2, LYS2 and the like.

A genetically modified host cell is a host cell that has been genetically modified with a subject nucleic acid or a subject recombinant vector. In many embodiments, a subject genetically modified host cell is an in vitro host cell. In other embodiments, a subject genetically modified host cell is an in vivo host cell. In other embodiments, a subject genetically modified host cell is part of a multicellular organism.

Host cells are in many embodiments unicellular organisms, or are grown in in vitro culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thennotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like. In some embodiments, the host cell is a eukaryotic cell other than a plant cell.

In other embodiments, the host cell is a plant cell. Plant cells include cells of monocotyledons ("monocots") and dicotyledons ("dicots").

In other embodiments, the host cell is a prokaryotic cell. Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270: 299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella* disenteriae. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some embodiments, the host cell is *Escherichia coli*.

In some embodiments, a subject genetically modified host cell is a plant cell. A subject genetically modified plant cell is useful for producing a selected isoprenoid compound in in vitro plant cell culture. Guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

A genetically modified host cell is useful for producing a biosynthetic product or a precursor biosynthetic product, where the level of the product or the precursor product produced in a genetically modified host cell is higher than the level of the product or the precursor product produced in a control host cell not genetically modified with a nucleic acid comprising a nucleotide sequence encoding a scaffold polypeptide. For example, the level of a producing a biosynthetic product or a precursor biosynthetic product produced in a genetically modified host cell is at least about 10%, at least about 20%, at least about 25%, at least about 30%, at least about 40%, at least about 50%, at least about 60%, at least about 70%, at least about 80%, at least about 90%, at least about 100% (or two-fold), at least about 2.5-fold, at least about 3-fold, at least about 5-fold, at least about 7-fold, at least about 10-fold, at least about 15-fold, at least about 20-fold, at least about 50-fold, at least about $10^2$-fold, at least about 500-fold, or at least about $10^3$-fold, or more, higher than the level in a control host cell not genetically modified with a nucleic acid comprising a nucleotide sequence encoding a scaffold polypeptide.

In some embodiments, the biosynthetic product or a precursor biosynthetic product is one that is not normally produced by a control host cell, e.g., the biosynthetic product or a precursor biosynthetic product is an exogenous product. In other embodiments, the biosynthetic product or a precursor biosynthetic product is one that is normally produced by the host cell, but is produced by a genetically modified host cell in amounts that are greater than the amount that would be produced by a control host cell. For example, in some embodiments, a biosynthetic product or a precursor biosynthetic product produced by a genetically modified host cell is produced in an amount that is at least about 10%, at least about 20%, at least about 25%, at least about 30%, at least about 40%, at least about 50%, at least about 60%, at least about 70%, at least about 80%, at least about 90%, at least about 100% (or two-fold), at least about 2.5-fold, at least about 3-fold, at least about 5-fold, at least about 7-fold, at least about 10-fold, at least about 15-fold, at least about 20-fold, at least about 50-fold, at least about $10^2$-fold, at least about 500-fold, at least about $10^3$-fold, at least about $5 \times 10^3$-fold, or at least about $10^4$-fold, or more, higher than the amount of the product produced in a control host cell, on a per cell basis or on a per cell culture (e.g., unit cell culture volume) basis or on a per cell mass (e.g., per $10^6$ cells) basis.

In some embodiments, a biosynthetic product or a precursor biosynthetic product produced by a genetically modified host cell is produced in an amount of from about 10 mg/L to about 50 g/L, e.g., from about 10 mg/L to about 25 mg/L, from about 25 mg/L to about 50 mg/L, from about 50 mg/L to about 75 mg/L, from about 75 mg/L to about 100 mg/L, from about 100 mg/L to about 250 mg/L, from about 250 mg/L to about 500 mg/L, from about 500 mg/L to about 750 mg/L, from about 750 mg/L to about 1000 mg/L, from about 1 g/L to about 1.2 g/L, from about 1.2 g/L to about 1.5 g/L, from about 1.5 g/L to about 1.7 g/L, from about 1.7 g/L to about 2 g/L, from about 2 g/L to about 2.5 g/L, from about 2.5 g/L to about 5 g/L, from about 5 g/L to about 10 g/L, from about 10 g/L to about 20 g/L, from about 20 g/L to about 30 g/L, from about 30 g/L to about 40 g/L, or from about 40 g/L to about 50 g/L, or more, on a cell culture basis.

Compositions Comprising a Genetically Modified Host Cell

The present invention further provides compositions comprising a genetically modified host cell. A composition comprises a genetically modified host cell, and will in some embodiments comprise one or more further components, which components are selected based in part on the intended use of the genetically modified host cell. Suitable components include, but are not limited to, salts; buffers; stabilizers; protease-inhibiting agents; nuclease-inhibiting agents; cell membrane- and/or cell wall-preserving compounds, e.g., glycerol, dimethylsulfoxide, etc.; nutritional media appropriate to the cell; and the like. In some embodiments, the cells are lyophilized.

Methods of Producing a Biosynthetic Pathway Product or Precursor

The present invention provides methods of producing a biosynthetic pathway product or biosynthetic pathway precursor, generally involving culturing a subject genetically modified host cell in a suitable medium and under suitable conditions to provide for production of the biosynthetic pathway product or biosynthetic pathway precursor. In some embodiments, the method is carried out in vitro (e.g., in a living cell cultured in vitro). In some of these embodiments, the host cell is a eukaryotic cell, e.g., a yeast cell. In other embodiments, the host cell is a prokaryotic cell.

A subject genetically modified host cell provides for enhanced production of a biosynthetic pathway product or biosynthetic pathway precursor, compared to a control, parent host cell not genetically modified with a nucleic acid comprising a nucleotide sequence encoding a scaffold polypeptide. Thus, e.g., production of a biosynthetic pathway product or biosynthetic pathway precursor is at least about 10%, at least about 20%, at least about 25%, at least about 30%, at least about 40%, at least about 50%, at least about 60%, at least about 70%, at least about 80%, at least about 90%, at least about 100% (or two-fold), at least about 2.5-fold, at least about 3-fold, at least about 5-fold, at least about 7-fold, at least about 10-fold, at least about 15-fold, at least about 20-fold, at least about 50-fold, at least about $10^2$-fold, at least about 500-fold, at least about $10^3$-fold, at least about $5 \times 10^3$-fold, or at least about $10^4$-fold, or more, higher in the genetically modified host cell, compared to the level of the product produced in a control parent host cell.

In some embodiments, a biosynthetic pathway product or a biosynthetic pathway precursor produced by a genetically modified host cell is produced in an amount of from about 10 mg/L to about 50 g/L, e.g., from about 10 mg/L to about 25 mg/L, from about 25 mg/L to about 50 mg/L, from about 50 mg/L to about 75 mg/L, from about 75 mg/L to about 100 mg/L, from about 100 mg/L to about 250 mg/L, from about 250 mg/L to about 500 mg/L, from about 500 mg/L to about 750 mg/L, from about 750 mg/L to about 1000 mg/L, from about 1 g/L to about 1.2 g/L, from about 1.2 g/L to about 1.5 g/L, from about 1.5 g/L to about 1.7 g/L, from about 1.7 g/L to about 2 g/L, from about 2 g/L to about 2.5 g/L, from about 2.5 g/L to about 5 g/L, from about 5 g/L to about 10 g/L, from about 10 g/L to about 20 g/L, from about 20 g/L to about 30 g/L, from about 30 g/L to about 40 g/L, or from about 40 g/L to about 50 g/L, or more, on a cell culture basis.

A subject genetically modified host cell can be cultured in vitro in a suitable medium and at a suitable temperature. The temperature at which the cells are cultured is generally from about 18° C. to about 40° C., e.g., from about 18° C. to about 20° C., from about 20° C. to about 25° C., from about 25° C. to about 30° C., from about 30° C. to about 35° C., or from about 35° C. to about 40° C. (e.g., at about 37° C.).

In some embodiments, a subject genetically modified host cell is cultured in a suitable medium (e.g., Luria-Bertoni broth, optionally supplemented with one or more additional agents, such as an inducer (e.g., where a nucleotide sequence encoding a biosynthetic pathway enzyme and/or a scaffold polypeptide is under the control of an inducible promoter)); and the biosynthetic pathway product or a biosynthetic pathway precursor is isolated from the cell culture medium and/or from cell lysates. In some embodiments, where one or more nucleotide sequences are operably linked to an inducible promoter, an inducer is added to the culture medium; and, after a suitable time, the product is isolated from the culture medium and/or from a cell lysate.

In some embodiment, the culture medium is supplemented with a substrate for the first enzyme in the biosynthetic pathway, where the substrate enters into the cell and is converted by the biosynthetic pathway into a product. In other embodiments, the substrate for the first enzyme in the biosynthetic pathway is made by the cell, and is converted by the biosynthetic pathway into a product.

In some embodiments, a subject genetically modified host cell is cultured in a suitable medium and the culture medium is overlaid with an organic solvent, e.g. dodecane, forming an organic layer. In these embodiments, the biosynthetic pathway product or biosynthetic pathway precursor produced by the genetically modified host cell partitions into the organic layer, from which it can be purified. In some embodiments, where one or more nucleotide sequences are operably linked to an inducible promoter, an inducer is added to the culture medium; and, after a suitable time, the product is isolated from the organic layer overlaid on the culture medium.

In some embodiments, the biosynthetic pathway product or biosynthetic pathway precursor will be separated from other products, macromolecules, etc., which may be present in the cell culture medium, the cell lysate, or the organic layer. Separation of the biosynthetic pathway product or biosynthetic pathway precursor from other products that may be present in the cell culture medium, cell lysate, or organic layer is readily achieved using, e.g., standard chromatographic techniques. Separation of the biosynthetic pathway product or biosynthetic pathway precursor from other products that may be present in the cell culture medium, cell lysate, or organic layer is readily achieved using, e.g., standard isolation techniques for small molecule products. For example, a method can involve pH adjustment and crystallization in organic solvent. Methods of isolating and purifying artemisinin, e.g., are known in the art; see, e.g., U.S. Pat. No. 6,685, 972.

In some embodiments, a biosynthetic pathway product or biosynthetic pathway precursor synthesized by a subject method is further chemically modified in one or more cell-free reactions.

In some embodiments, the biosynthetic pathway product or biosynthetic pathway precursor is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of a biosynthetic pathway product or biosynthetic pathway precursor refers to a biosynthetic pathway product or biosynthetic pathway precursor that is free from other biosynthetic pathway product or biosynthetic pathway precursor, macromolecules, contaminants, etc.

In some embodiments, the biosynthetic pathway precursor is mevalonate. In some embodiments, the biosynthetic pathway product is an artemisinin precursor (e.g., artemisinic alcohol, artemisinic aldehyde, artemisinic acid, etc.). In some of these embodiments, the artemisinin precursor product is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of an artemisinin precursor refers to an artemisinin precursor that is free from side products, macromolecules, contaminants, etc.

Biosynthetic Pathway Products and Precursors

As noted above, a subject method provides for production of a biosynthetic pathway product and/or a precursor of a biosynthetic pathway product in a subject genetically modified host cell. A precursor of a biosynthetic pathway product is also referred to as an "intermediate." Exemplary intermediates include, but are not limited to, isoprenoid precursors; alkaloid precursors; phenylpropanoid precursors; flavonoid precursors; steroid precursors; polyketide precursors; macrolide precursors; sugar alcohol precursors; phenolic compound precursors; and the like. See, e.g., Hwang et al. ((2003) *Appl. Environ. Microbiol.* 69:2699-2706; Facchini et al. ((2004) *TRENDS Plant Sci.* 9:116.

Biosynthetic pathway products of interest include, but are not limited to, isoprenoid compounds, alkaloid compounds, phenylpropanoid compounds, flavonoid compounds, steroid compounds, polyketide compounds, macrolide compounds, sugar alcohols, phenolic compounds, and the like.

Alkaloid compounds are a large, diverse group of natural products found in about 20% of plant species. They are generally defined by the occurrence of a nitrogen atom in an oxidative state within a heterocyclic ring. Alkaloid compounds include benzylisoquinoline alkaloid compounds, indole alkaloid compounds, isoquinoline alkaloid compounds, and the like. Alkaloid compounds include monocyclic alkaloid compounds, dicyclic alkaloid compounds, tricyclic alkaloid compounds, tetracyclic alkaloid compounds, as well as alkaloid compounds with cage structures. Alkaloid compounds include: 1) Pyridine group: piperine, coniine, trigonelline, arecaidine, guvacine, pilocarpine, cytisine, sparteine, pelletierine; 2) Pyrrolidine group: hygrine, nicotine, cuscohygrine; 3) Tropine group: atropine, cocaine, ecgonine, pelletierine, scopolamine; 4) Quinoline group: quinine, dihydroquinine, quinidine, dihydroquinidine, strychnine, brucine, and the veratrum alkaloids (e.g., veratrine, cevadine); 5) Isoquinoline group: morphine, codeine, thebaine, papaverine, narcotine, narceine, hydrastine, and berberine; 6) Phenethylamine group: methamphetamine, mescaline, ephedrine; 7) Indole group: tryptamines (e.g., dimethyltryptamine, psilocybin, serotonin), ergolines (e.g., ergine, ergotamine, lysergic acid, etc.), and beta-carbolines (e.g., harmine, yohimbine, reserpine, emetine); 8) Purine group: xanthines (e.g., caffeine, theobromine, theophylline); 9) Terpenoid group: aconite alkaloids (e.g., aconitine), and steroids (e.g., solanine, samandarin); 10) Betaine group: (quaternary ammonium compounds: e.g., muscarine, choline, neurine); and 11) Pyrazole group: pyrazole, fomepizole. Exemplary alkaloid compounds are morphine, berberine, vinblastine, vincristine, cocaine, scopolamine, caffeine, nicotine, atropine, papaverine, emetine, quinine, reserpine, codeine, serotonin, etc. See, e.g., Facchini et al. ((2004) *Trends Plant Science* 9:116).

The term "isoprenoid precursor compound" is used interchangeably with "isoprenoid precursor substrate" to refer to a compound that is a product of the reaction of a terpene synthase on a polyprenyl diphosphate. The product of action of a terpene synthase (also referred to as a "terpene cyclase") reaction is the so-called "terpene skeleton." In some embodiments, the isoprenoid-modifying enzyme catalyzes the modification of a terpene skeleton, or a downstream product thereof. Thus, in some embodiments, the isoprenoid precursor is a terpene skeleton. Isoprenoid precursors include monoterpenes, diterpenes, triterpenes, and sesquiterpenes.

Monoterpenes include, but are not limited to, Acyclic monoterpenes, Dimethyloctanes, Menthanes, Irregular Monoterpenoids, Cineols, Camphanes, Isocamphanes, Monocyclic monoterpenes, Pinanes, Fenchanes, Thujanes, Caranes, Ionones, Iridanes, and Cannabanoids. Exemplary monoterpene substrates, intermediates, and products include, but are not limited to, limonene, citranellol, geraniol, menthol, perillyl alcohol, linalool, and thujone.

Diterpene include, but are not limited to, Acyclic Diterpenoids, Bicyclic Diterpenoids, Monocyclic Diterpenoids, Labdanes, Clerodanes, Taxanes, Tricyclic Diterpenoids, Tetracyclic Diterpenoids, Kaurenes, Beyerenes, Atiserenes, Aphidicolins, Grayanotoxins, Gibberellins, Macrocyclic Diterpenes, and Elizabethatrianes. Exemplary diterpene substrates, intermediates, and products include, but are not limited to, casbene, eleutherobin, paclitaxel, prostratin, and pseudopterosin.

Triterpene include, but are not limited to, arbrusideE, bruceantin, testosterone, progesterone, cortisone, and digitoxin.

Sesquiterpene include, but are not limited to, Farnesanes, Monocyclofarnesanes, Monocyclic sesquiterpenes, Bicyclic sesquiterpenes, Bicyclofarnesanes, Bisbolanes, Santalanes, Cupranes, Herbertanes, Gymnomitranes, Trichothecanes, Chamigranes, Carotanes, Acoranes, Antisatins, Cadinanes, Oplopananes, Copaanes, Picrotoxanes, Himachalanes, Longipinanes, Longicyclanes, Caryophyllanes, Modhephanes, Siphiperfolanes, Humulanes, Intergrifolianes, Lippifolianes, Protoilludanes, Illudanes, Hirsutanes, Lactaranes, Sterpuranes, Fomannosanes, Marasmanes, Germacranes, Elemanes, Eudesmanes, Bakkanes, Chilosyphanes, Guaianes, Pseudoguaianes, Tricyclic sesquiterpenes, Patchoulanes, Trixanes, Aromadendranes, Gorgonanes, Nardosinanes, Brasilanes, Pinguisanes, Sesquipinanes, Sesquicamphanes, Thujopsanes, Bicylcohumulanes, Alliacanes, Sterpuranes, Lactaranes, Africanes, Integrifolianes, Protoilludanes, Aristolanes, and Neolemnanes. Exemplary sesquiterpene substrates include, but are not limited to, amorphadiene, alloisolongifolene, (−)-α-trans-bergamotene, (−)-β-elemene, (+)-germacrene A, germacrene B, (+)-γ-gurjunene, (+)-ledene, neointermedeol, (+)-β-selinene, and (+)-valencene.

A subject method is useful for production of a variety of isoprenoid compounds, including, but not limited to, artemisinic acid (e.g., where the sesquiterpene substrate is amorpha-4,11-diene), alloisolongifolene alcohol (e.g., where the substrate is alloisolongifolene), (E)-trans-bergamota-2,12-dien-14-ol (e.g., where the substrate is (−)-α-trans-bergamotene), (−)-elema-1,3,11(13)-trien-12-ol (e.g., where the substrate is (−)-β-elemene), germacra-1(10),4,11(13)-trien-12-ol (e.g., where the substrate is (+)-germacrene A), germacrene B alcohol (e.g., where the substrate is germacrene B), 5,11(13)-guaiadiene-12-ol (e.g., where the substrate is (+)-γ-gurjunene), ledene alcohol (e.g., where the substrate is (+)-ledene), 4β-H-eudesm-11(13)-ene-4,12-diol (e.g., where the substrate is neointermedeol), (+)-β-costol (e.g., where the substrate is (+)-β-selinene, and the like; and further derivatives of any of the foregoing.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Production of Mevalonate

Two strategies for balancing pathway flux have been successfully applied: modulating the expression levels of individual enzymes (via promoter strengths, ribosome binding site strengths, plasmid copy number, tunable intergenic regions controlling mRNA processing, etc.) and improving turnover activities of rate-limiting enzymes by directed evolution. Here we describe a distinct, but complementary, strategy for increasing overall pathway flux while simultaneously reducing metabolic loads. Pathway enzymes are co-localized to synthetic complexes in a programmable manner using engineered interactions between well-characterized protein-protein interaction domains and their specific ligands. Using this approach, enzyme assembly lines can be constructed in a generalizeable, scalable manner to increase the effective concentration of intermediate metabolites while maintaining their levels below toxicity limits. In addition, relative fluxes of individual enzymes can be balanced for optimal production yields by varying the number of interaction domain repeats targeting independent enzymes to the synthetic complex.

The scaffolding strategy described herein includes certain features of natural systems exhibiting substrate channeling. Substrate channeling has several potential advantages: 1) reducing the loss of intermediates to diffusion or competing pathways, 2) protecting unstable intermediates from solvent and/or decreasing the transit time of intermediates, and 3) circumventing unfavorable equilibria and kinetics imposed by bulk-phase metabolite concentrations. Tryptophan synthase and carbamoyl phosphate synthetase provide two illustrative examples of substrate channeling. Crystal structures and biochemical analysis have shown long tunnels that protect the reactive intermediates from the bulk solution. Polyketide synthases offer another interesting case of substrate channeling—modules consisting of assembly lines of catalytic activities where substrates are directly tethered to, and processively carried through, the enzyme modules via thioester linkages. These natural examples illustrate two approaches of substrate channeling: sequestration versus covalent tethering of intermediates. In this study, we aimed to approximate the behavior of these elegant substrate channeling enzyme systems, albeit with a much simpler design, in order to improve pathway flux in a programmable manner.

The three-enzyme pathway that produces mevalonate from acetyl-CoA was selected as a model system. Mevalonate is a precursor for synthesis of the large isoprenoid family, members of which have therapeutic and commercial value, including the anti-malarial drug artemisinin. Most important for this study, the mevalonate biosynthetic pathway is not endogenous to the production host, *Escherichia coli* (*E. coli*), and heterologous expression can result in flux imbalances with high metabolic load. The first enzyme, acetoacetyl-CoA thiolase (AtoB), is native to *E. coli*, while the second and third enzymes, hydroxy-methylglutaryl-CoA synthase (HMGS) and hydroxy-methylglutaryl-CoA reductase (HMGR), were imported from *Saccharomyces cerevisiae* and codon-optimized for expression in *E. coli*. The genes encoding the pathway enzymes were placed under the heterologous transcriptional regulation of inducible promoter systems, and modular control was gained by employing machinery evolved for signal processing in metazoan cells (FIG. 1). These machineries (protein-protein interaction domains and their ligands) are used in many different combinations in natural proteins to achieve different behaviors and in synthetic proteins capable of sophisticated gating. Thus, these domain/ligands have proven to be engineerable, as well as adaptable, and therefore provide excellent modular parts for building synthetic scaffolds. Importantly, since they are not naturally present in E. coli, the interaction domain/ligand pairs should be programmable with minimal cross-talk with the prokaryotic cellular milieu.

Figure 2A:
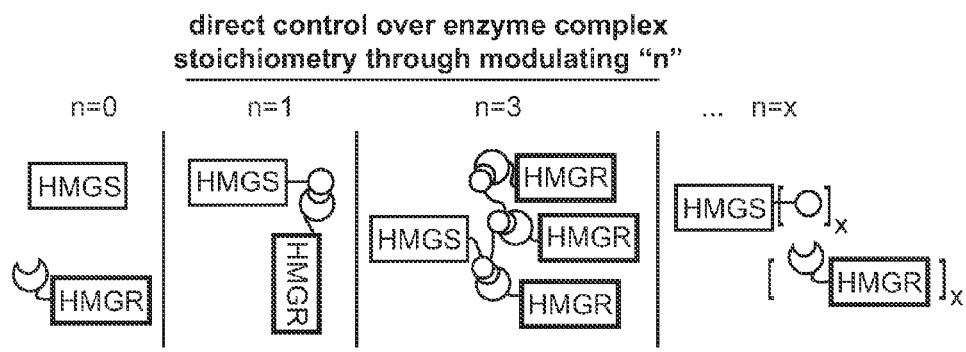
FIGS. 2A-C provide: a schematic depiction of a method for control over enzyme stoichiometry (FIG. 2A); results of a GST pull-down experiment using HMGS with 0, 1, or 6 SH3 interaction motifs introduced at the C-terminus of the enzyme, and HMGR with an SH3 domain introduced at the N-terminus of the enzyme (FIG. 2B); and mevalonate production in *E. coli* genetically modified with a nucleic acid encoding HMGS with 0, 1, 3, 6, or 12 SH3 ligands introduced at the C-terminus of the enzyme, and HMGS with an SH3 domain introduced at the N-terminus of the enzyme (FIG. 2C).
Figure 2B:
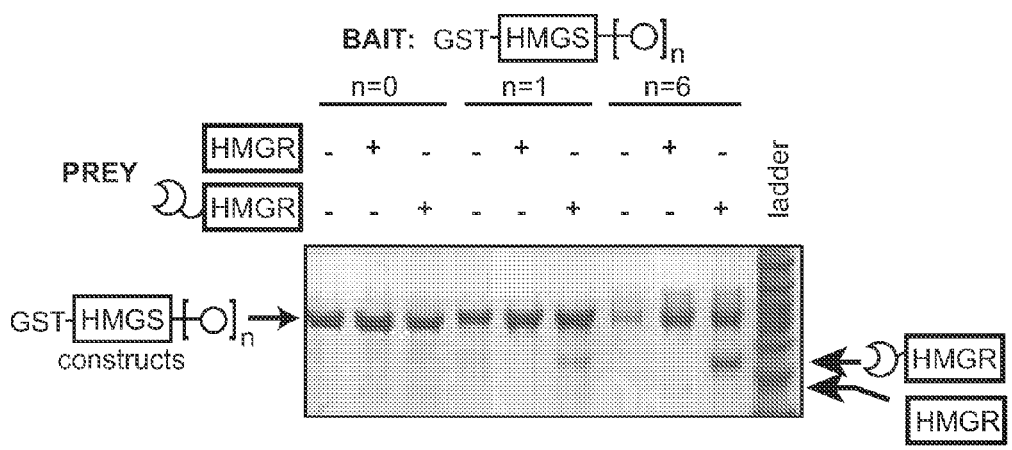

As a direct test of engineered enzyme co-recruitment, the bottleneck enzymatic step of the mevalonate biosynthetic pathway (HMGR-catalyzed turnover of HMG-CoA to mevalonate) was targeted for flux improvement. A synthetic complex of HMGS and HMGR was created by recombining a varying number of SH3 (Src Homology 3 domain from the adapter protein CRK) interaction ligands to the C-terminus of HMGS and recombining an SH3 domain to the N-terminus of HMGR (FIG. 2a). This simple design also allowed for control over the relative ratio of these two enzymes at the resultant complex. The ability of these proteins to interact in an SH3-dependent manner was probed in a GST pull-down experiment (FIG. 2b). An N-terminal GST-tagged HMGS with 0, 1, or 6 C-terminal SH3 peptide ligands ($K_d$=0.1 μM) was used as bait. As prey, an SH3 domain was recombined to the N-terminus of HMGR and compared to HMGR alone. No significant interaction was observed between HMGS and HMGR without engineered SH3 interactions. However, HMGR with an N-terminal SH3 domain was pulled down by GST-tagged HMGS in a ligand-dependent manner. An observable amount of HMGR was pulled-down when a single ligand was tethered to HMGS, but significantly more was pulled-down when six ligands were tethered to HMGS. Thus, the relative stoichiometries of these two enzymes were controlled at the complex by varying the number of interaction ligands tethered to HMGS.

Figure 2C:
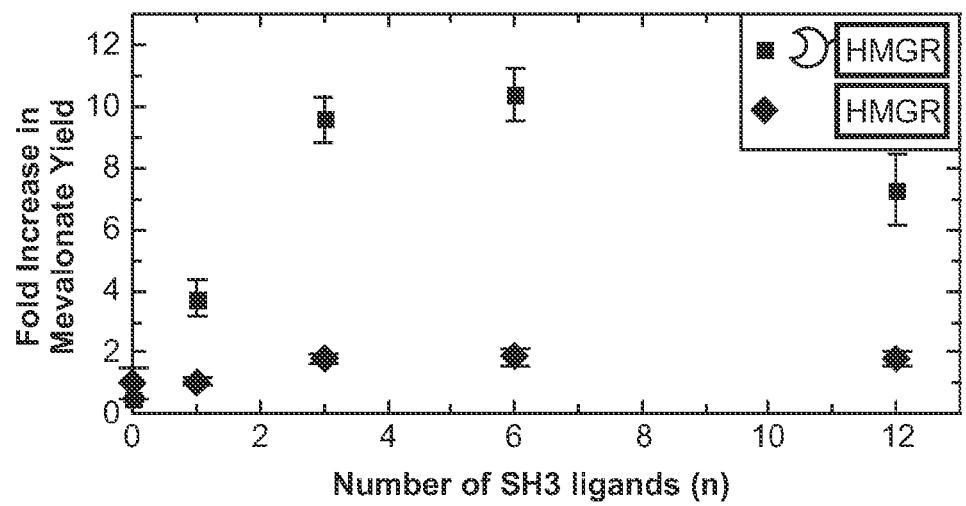

The efficacy of improving mevalonate pathway flux in vivo was tested. To gain maximum control over expression levels, the genes encoding the first two enzymes of the pathway (AtoB and HMGS) were placed under control of an arabinose-inducible promoter ($P_{BAD}$), and the gene encoding HMGR was placed under expression control of a tetracycline-inducible promoter ($P_{tet}$). All experiments were conducted with high expression levels of AtoB and HMGS, but low expression levels of the flux-limiting HMGR enzyme, to demonstrate that this bottleneck in the pathway could be overcome via synthase/reductase co-recruitment. Varying numbers of SH3 peptide ligands (0, 1, 3, 6, or 12), separated by flexible glycine-serine linkers, were recombined to the C-terminus of HMGS and co-expressed with HMGR either alone, or with an N-terminal SH3 domain tag. Improvement in mevalonate production was seen for engineered co-recruitment of HMGS/R enzymes (FIG. 2c). As expected, this improvement was dependent on the presence of both the SH3 domain and ligand and showed a dependence on the number of interactions.

Interestingly, mevalonate production reached a maximum ~10-fold improvement with 6 possible interactions, but reduced somewhat (to 7-fold) when the number of possible interactions was further increased. Three explanations are possible: 1) the increased local concentration effect from enzyme co-localization may be diminished with increasing number of ligands spatially separating the co-localized enzymes when the pool of HMGR is insufficient to saturate all of the binding sites, 2) the limiting HMGR is sequestered such that it is unevenly distributed among the HMGS molecules, and/or 3) addition of too many SH3 ligands leads to HMGS misfolding. Thus, mevalonate yields can be improved through both engineered co-localization of HMGS and HMGR as well as optimization of the number of introduced interaction ligands.

Figure 3A:
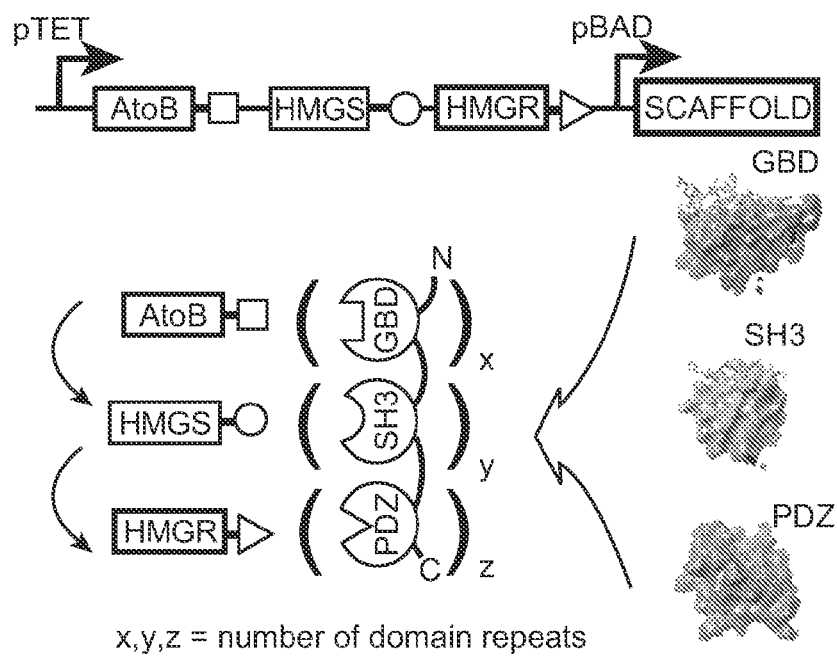
FIGS. 3A-C depict use of a scaffold with interaction motifs and mevalonate pathway enzymes comprising corresponding peptide ligands.

The scalability of the co-recruitment strategy was tested by building separate scaffold devices capable of co-localizing multiple enzymes. Scaffolds provide a means for physically separating the binding elements for design control from the catalytic activities. Thus, the only modification to the enzyme necessary for gaining modular control over complex formation is the addition of a single interaction ligand to each enzyme. A peptide ligand specific for a corresponding protein-protein interaction domain was recombined to the C-terminus of each enzyme of the mevalonate biosynthetic pathway (FIG. 3a). Scaffolds were built by tethering together, via flexible nine amino acid glycine-serine linkers, different numbers of three protein-protein interaction domains from metazoan genomes: the GTPase Binding Domain (GBD) from the actin polymerization switch N-WASP, the SH3 domain, and the PSD95/DlgA/Zo-1 (PDZ) domain from the adaptor protein syntrophin (see Table 1, below).

TABLE 1

| Protein-protein Interaction Domains | Source | Residues | |
|---|---|---|---|
| PDZ | Mouse α-syntrophin (syn) | 77-171 | |
| GBD | rat N-WASP | 196-274 | |
| SH3 | mouse Crk | 134-191 | |
| Interaction ligands | Sequence | Partner | Kd (μM) |
| PDZ lig. | GVKESLV; SEQ ID NO: 25 | Syn PDZ | 8 |
| GBD lig. | LVGALMHVMQKRSRAIHSSD EGEDQAGDEDED; SEQ ID NO: 30 | WASP GBD | 1 |
| SH3 lig. | PPPALPPKRRR; SEQ ID NO: 22 | Crk SH3 | 0.1 |

Intramolecular ligand affinities for partner domains are reported as measured in trans.

For PDZ/mouse α-syntrophin, see Schultz et al. (1998) Nat Struct Biol 5:19-24; for GBD/rat N-WASP, see Kim et al. (2000) Nature 404:151-8; for SH3/mouse Crk, see Wu et al. (1995) Structure 3:215-26.

By varying the number of repeats of these interaction domains, the ratio of individual pathway enzymes co-localized to the resultant complex could be controlled. Scaffolds were built with a single GBD domain for recruiting AtoB and varying numbers of SH3 and PDZ domains for recruiting HMGS and HMGR, respectively. A matrix of scaffolds was made with the architecture (N-terminal to C-terminal) of $GBD_xSH3_yPDZ_z$ where x=1 and y and z were varied to be 1, 2, or 4. For separate inducible control, the pathway enzymes were placed under transcriptional control of the tetracycline-inducible promoter ($P_{tet}$), and the scaffolds were under transcriptional control of the arabinose-inducible promoter ($P_{BAD}$). In an effort to lower the metabolic load imposed on the production host, mevalonate production experiments were conducted with low expression levels of the mevalonate pathway enzymes (7 nM aTc) and a high scaffold expression level (250 μM arabinose) to improve pathway efficiency.

Figure 3B:
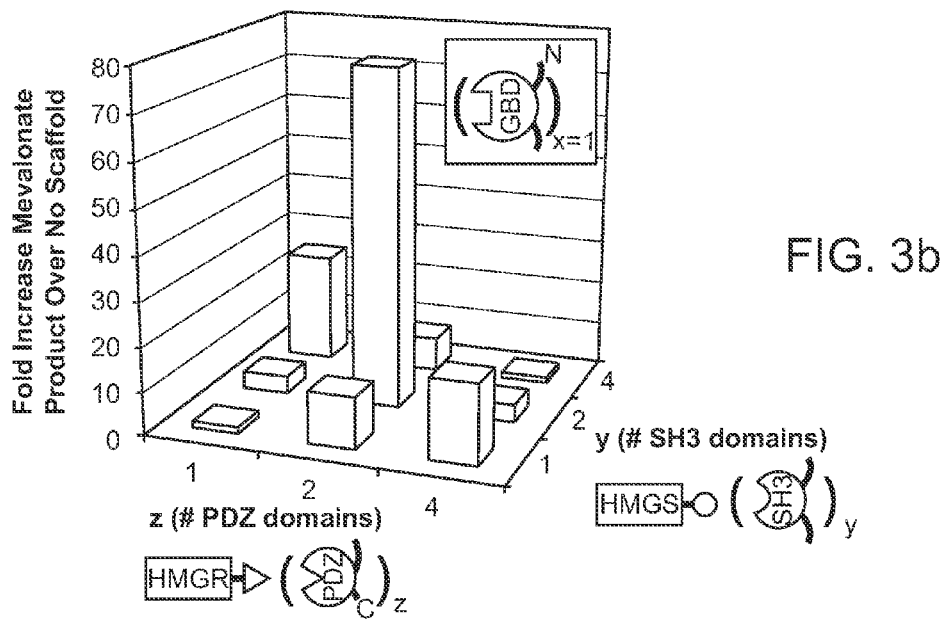
Figure 3C:
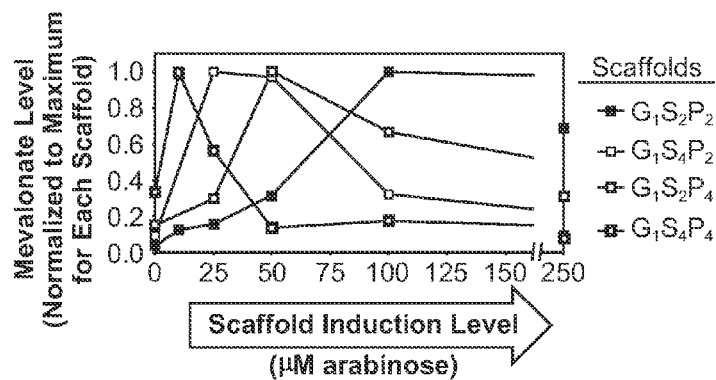

Mevalonate yields were measured for the unscaffolded pathway ($GBD_0SH3_0PDZ_0$ or $G_0S_0P_0$), and improvements in production were plotted for each scaffold (FIG. 3b). Remarkably, a 77-fold increase in mevalonate production was observed for the optimal scaffold ($G_1S_2P_2$). Yield improvements were dependent on the number of interaction domain repeats in the scaffolds: varying the scaffold composition by a single domain often resulted in greater than an order of magnitude difference in mevalonate production. For example, scaffolds $G_1S_2P_2$ and $G_1S_1P_2$ differ by only one SH3 domain, yet produced dramatically different mevalonate yields: 77-fold versus 4-fold, respectively. Further, scaffolds with differing numbers of interaction domain repeats varied in their flux-enhancing profiles as the inducer was titrated to modulate scaffold expression (FIG. 3c). Scaffolds with higher numbers of domain repeats exhibited optimal mevalonate production at lower scaffold expression levels while scaffolds with fewer numbers of domain repeats showed optimal mevalonate production at higher concentrations of inducer for scaffold expression. Scaffolds with intermediate numbers of interaction domains show optimal activities at intermediate expression levels. At high concentrations of scaffold, non-functional scaffold: enzyme stoichiometries can exist where scaffold sequesters rather than co-localizes enzymes.

The role of domain orientation in scaffold architecture was investigated by rearranging the interaction domains of the optimized scaffold $G_1S_2P_2$ to $G_1S_1P_2S_1$ and $G_1S_1P_1S_1P_1$ (see FIG. 10). Compared to the optimal scaffold $G_1S_2P_2$, scaffolds $G_1S_1P_2S_1$ and $G_1S_1P_1S_1P_1$ showed marked decreases in mevalonate production; 10-fold and 22-fold higher yields than the unscaffolded pathway, respectively, as opposed to the 77-fold improvement with $G_1S_2P_2$. Similarly, the effect of scaling the number of enzymes recruited to the scaffold was investigated by making scaffolds that recruited only HMGS and HMGR (see FIG. 11). Enhancement of mevalonate biosynthesis was greater with scaffolds built to recruit all three enzymes than for those recruiting only HMGS/R (77-fold versus 8.5-fold). Thus, both the number of interaction domains targeting the enzymes to the scaffold and their orientation had dramatic impacts on their ability to increase pathway flux.

The role of scaffolding in flux enhancement was verified through a series of control experiments. First, a competing PDZ ligand was incorporated into the mevalonate pathway operon as a GST fusion and co-expressed with scaffold $G_1S_2P_2$ ($G_1S_2P_2$-competitor1 in FIG. 9a). As expected, yields were lower than the same construct lacking the competitive PDZ ligand ($G_1S_2P_2$). Mevalonate production was further decreased when the expression level of the GST-tagged PDZ ligand was increased by driving expression with $P_{BAD}$ on a high copy plasmid ($G_1S_2P_2$-competitor2). To verify that the scaffolding effect depends upon the peptide ligands recombined to each enzyme, they were removed ($G_1S_2P_2\Delta$ligands); a dramatic decrease in mevalonate production, compared to $G_1S_2P_2$, was observed. Recombining the peptide ligands to the pathway enzymes did seem to lower their collective activities somewhat as $G_1S_2P_2\Delta$ligands (without peptide ligands) produced approximately 7.5-fold higher mevalonate yields than $G_0S_0P_0$ or the control where instead of a scaffold, GFP was expressed ($G_0S_0P_0$-GFP). However, this loss of activity was more than compensated for via scaffolding ($G_1S_2P_2$). The ability to tag enzymes with interaction ligands without perturbing function will be protein-dependent and may require searching for accommodating locations for peptide insertions in other enzyme structures.

Figure 13:
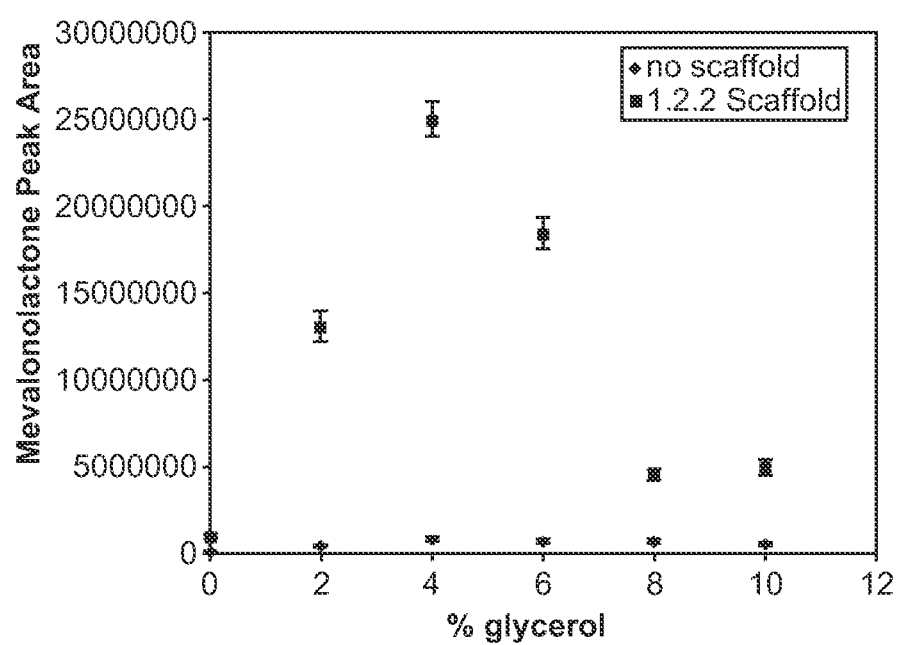
FIG. 13 depicts glycerol dependence of mevalonate product enhancement.

A practical advantage of scaffolding is the improvement in pathway efficiency, allowing equivalent or higher yields to be achieved at lower enzyme expression levels than without the scaffold. Even at saturating inducer concentrations, the unscaffolded pathway ($G_0S_0P_0$) did not reach the mevalonate yields of the scaffolded pathway ($G_1S_2P_2$) under basal expression levels (FIG. 9b). These scaffold-dependent increases in mevalonate production decreased as expression of pathway enzymes increased, suggesting the concentration of scaffold was not sufficient to maintain function with high pathway enzyme concentrations. Similarly, the cell cultures with the scaffolded pathway saturated at grew to higher optical densities than those harboring the non-scaffolded pathway when pathway enzyme expression levels were low (see FIG. 12). However, this improvement in cell growth was not maintained when pathway enzyme expression was increased. In this manner, the metabolic load introduced with an engineered metabolic pathway can be significantly reduced by both increasing the efficiency of the pathway and lowering the necessary expression levels of the pathway enzymes. Further supporting this scaffold-dependent improvement in pathway efficiency is the observation that mevalonate yields improved dramatically when the medium was supplemented with high concentrations of glycerol, but only when the pathway was scaffolded by $G_1S_2P_2$ (FIG. 13). Thus, scaffolds allowed the pathway to better utilize the increased carbon substrate, allowing higher product yields to be achieved with lower enzyme expression and decreasing the metabolic burden on the production host.

In this study, the naturally-evolved modularity of protein-protein interaction domains was employed to facilitate the rapid design and optimization of flux-increasing scaffolds. This strategy was inspired by natural biosynthetic machines (e.g., polyketide synthases, fatty acid synthases, and non-ribosomal peptide synthases) that produce small molecules by channeling intermediates iteratively through assembly lines of catalytic activities. Although simpler than these elegant natural systems, the modular design of the scaffold strategy described herein is programmable, scalable, and generalizeable. Importantly, scaffolding presents a strategy that can complement conventional strategies for balancing enzymatic activities for achieving increased product yields. The modular scaffold design facilitated the rapid optimization of pathway flux. This modularity provides programmability over the stoichiometry of enzymes recruited to the functional complex as well as scalability for increasing the number of enzymes in the pathway that are scaffolded. Since this design does not depend on structural characteristics of an enzyme, other than the ability to tether a short peptide ligand without perturbing activity, it should prove to be generalizeable to other pathways.

FIGS. 1A-C. Employing metazoan machinery for modular control over pathway flux. (a)

The genes encoding the mevalonate pathway enzymes (HMGS and HMGR) were taken from yeast (*Saccharomyces cerevisiae*) and transformed into *Escherichia coli* along with the *E. coli* gene encoding AtoB. These enzymes have different levels of activity, creating a bottleneck and, as a result, accumulation of the intermediate HMG-CoA that is toxic to *E. coli* at high concentrations. (b) Protein-protein interaction domains and ligands from metazoan cells (mouse SH3 and PDZ domains and rat GBD) were used to design regulation machinery and transformed into these same *E. coli* cells. Thus, both the mevalonate pathway enzymes and the regulation machinery are heterologous to *E. coli*. (c) The scaffolded pathway is more efficient as a result of co-localizing the mevalonate enzymes to the same complex as well as optimizing the enzyme stoichiometry to balance the units of activity at the complex.

FIGS. 2A-C. Direct control over enzyme stoichiometry of a synthetic complex can be introduced with heterologous protein-protein interaction domain/ligands. (a) A varying number of SH3 ligands were recombined to the C-terminus of HMGS, and an SH3 domain was recombined to the N-terminus of HMGR. (b) A GST pull-down was performed using HMGS bait with 0, 1, or 6 SH3 ligands and HMGR prey with and without an N-terminal SH3 domain. An interaction was only observed when both interaction partners were present and increased amounts of prey were pulled-down as the number of ligands was increased. (c) Mevalonate production increased as the number of ligands recombined to HMGS was increased until it reached a maximum of approximately 10-fold with 6 ligands. Improvements in mevalonate yield over that from the unscaffolded pathway decreased to approximately 7-fold when the number of ligands was further increased to 12. These significant yield increases required the recombination of a corresponding SH3 domain to HMGR. Error bars show 1 SD from an average of three separate experiments.

FIGS. 3A-C. Modular control over metabolic pathway flux was gained via synthetic scaffolds built from modular protein-protein interaction domains. (a) The mevalonate pathway was placed under expression control of $P_{tet}$, and expression of the synthetic scaffolds was controlled by $P_{BAD}$. The synthetic scaffolds were constructed with three protein-protein interaction domains (GBD, SH3, and PDZ) where x, y, and z represents the number of repeats of these domains, respectively. (b) A matrix of nine scaffolds exhibited dramatic differences in mevalonate product yields. Optimizing the relative number of recruitment domains ($GBD_1SH3_2PDZ_2$ or $G_1S_2P_2$) for maximum pathway flux resulted in a 77-fold increase in product yield compared to the non-scaffolded pathway ($G_0S_0P_0$). Improvements in mevalonate yields were strongly dependent on scaffold architecture. (c) The scaffold induction level for optimal mevalonate production is dependent on the number of interaction domains. Scaffolds with higher numbers of interaction domain repeats ($G_1S_4P_4$) showed optimal mevalonate production at lower scaffold inducer concentrations than scaffolds with fewer domain repeats ($G_1S_2P_2$). Scaffolds with intermediate numbers of repeats ($G_1S_4P_2$ and $G_1S_2P_4$) showed optimal production at intermediate inducer concentrations.

Figure 6:
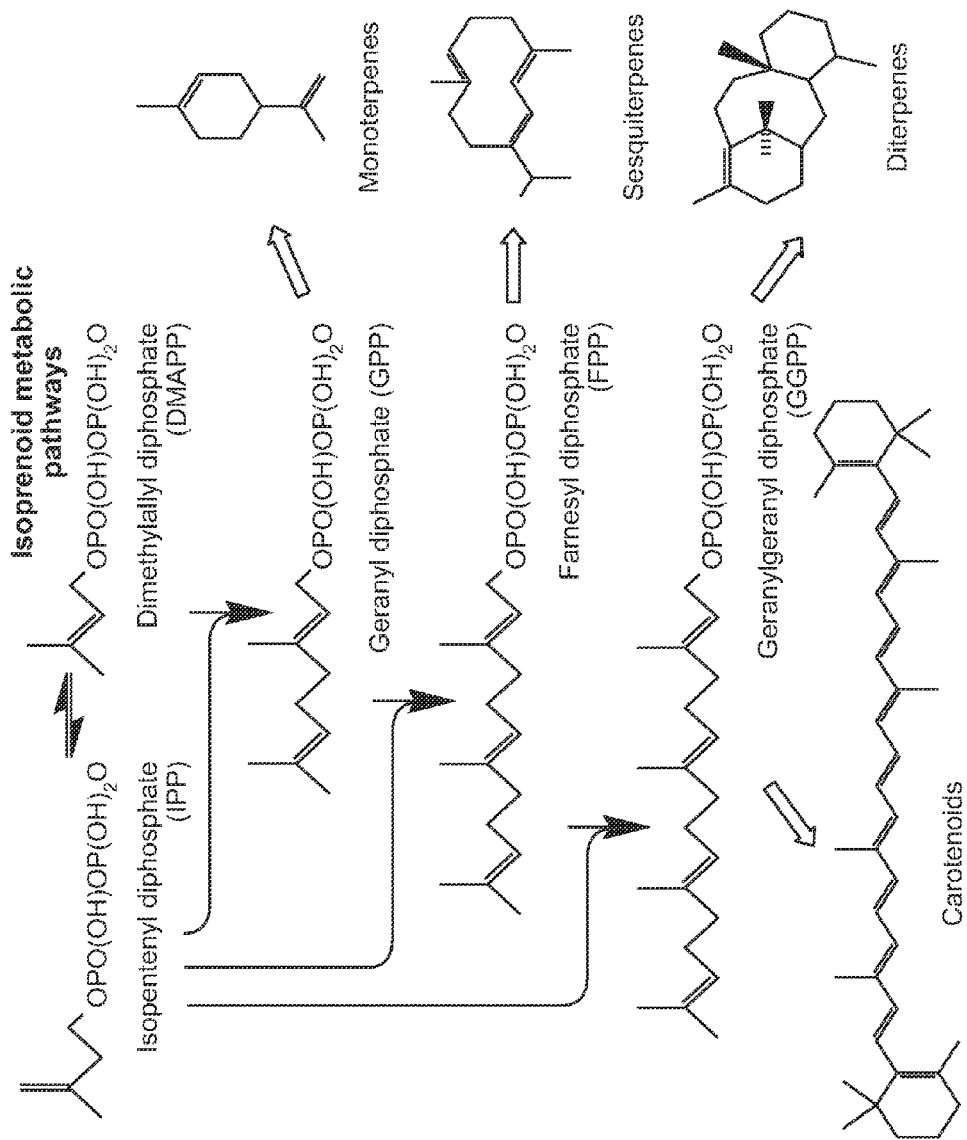
FIG. 6 is a schematic representation of isoprenoid metabolic pathways that result in the production of the isoprenoid biosynthetic pathway intermediates polyprenyl diphosphates geranyl diphosphate (GPP), farnesyl diphosphate (FPP), and geranylgeranyl diphosphate (GGPPP), from isopentenyl diphosphate (IPP) and dimethylallyl diphosphate (DMAPP).
Figure 7:
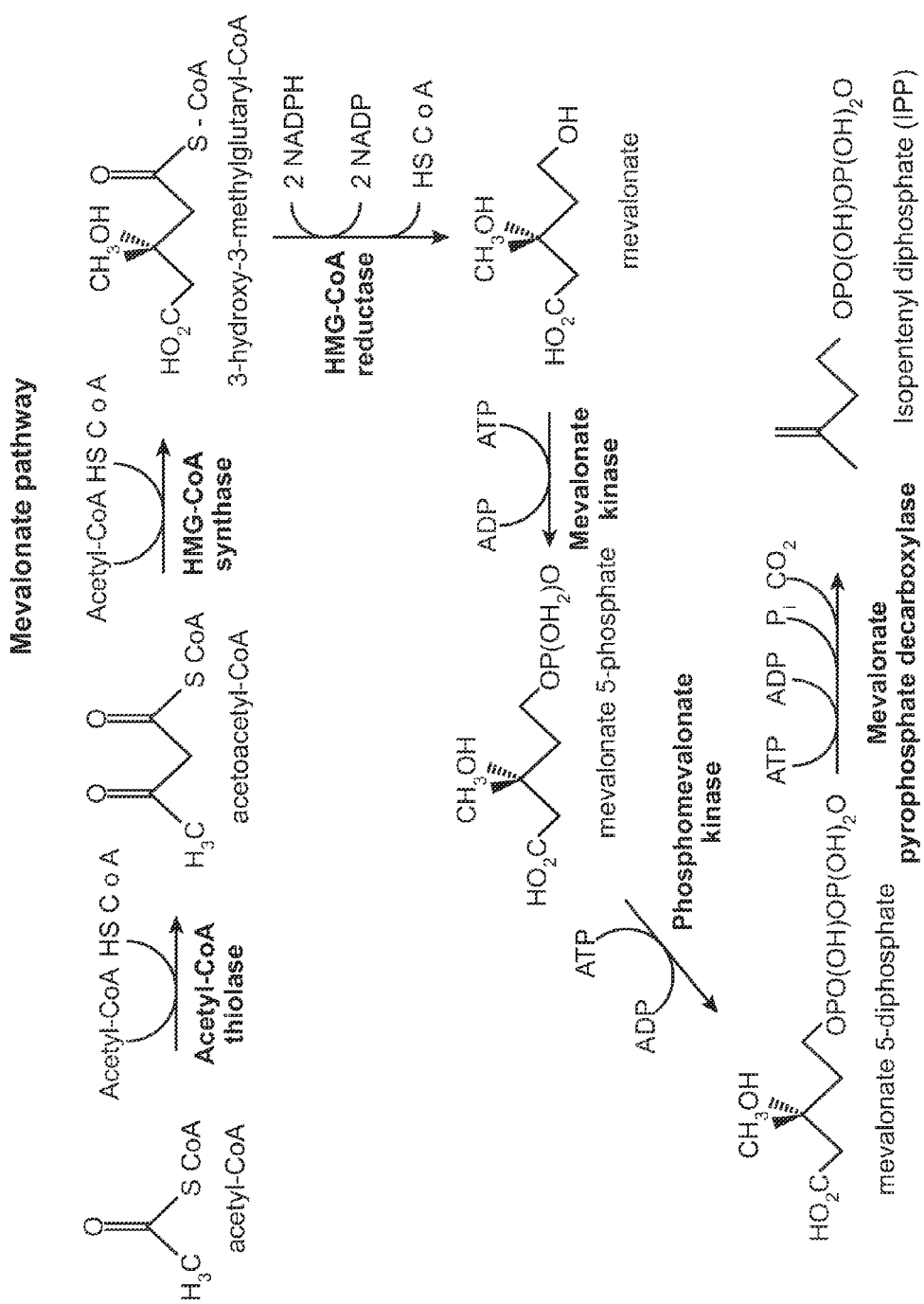
FIG. 7 is a schematic representation of the mevalonate (MEV) pathway for the production of IPP.

Amino acid sequences of chimeric mevalonate pathway enzymes are provided in FIGS. 4A and 4B. Amino acid sequences of exemplary scaffolds are provided in FIGS. 5A and 5B. FIGS. 6-8 depict pathways for synthesizing IPP and downstream isoprenoid products.

Figure 9A:
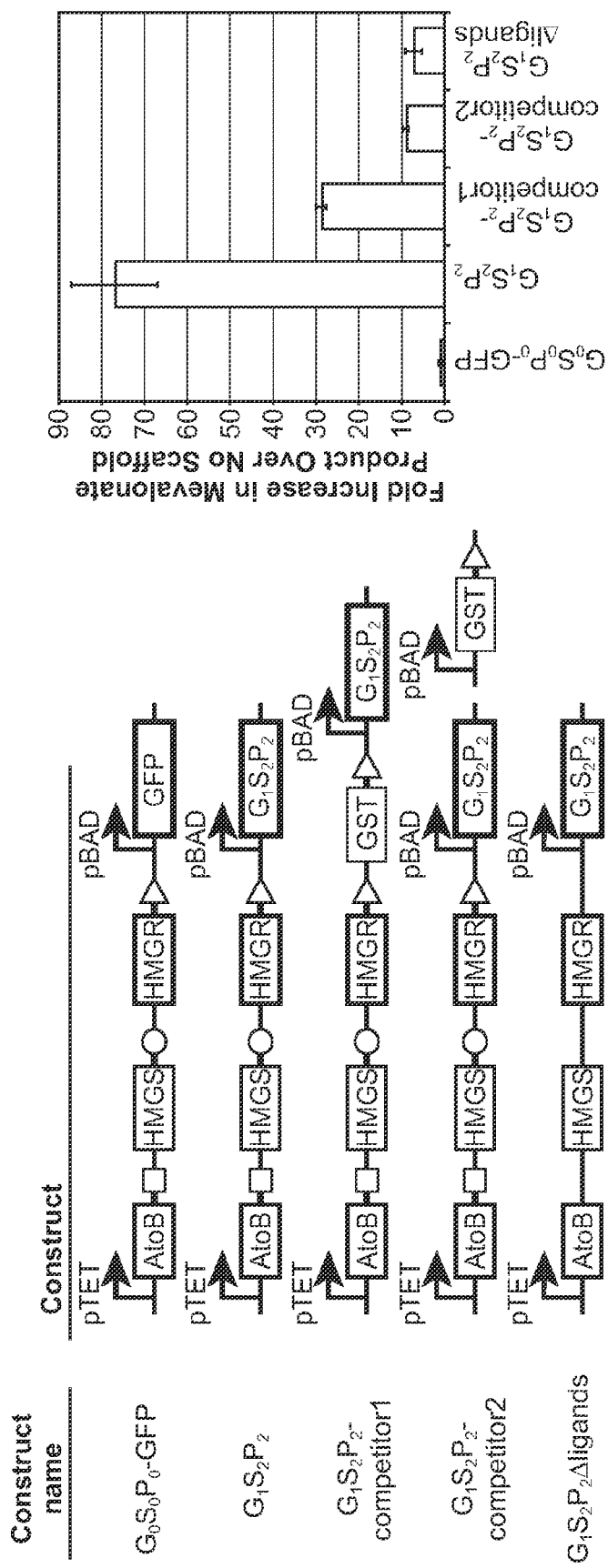

FIGS. 9A-C. Dependence of scaffold in enhancement in mevalonate production. (a) Mevalonate production from the optimal scaffold $G_1S_2P_2$ was compared to that from control constructs ($G_0S_0P_0$-GFP, $G_1S_2P_2$-competitor1, $G_1S_2P_2$-competitor2, $G_1S_2P_2\Delta$ligands). Expressing the green fluorescent protein ($G_0S_0P_0$-GFP) instead of a scaffold produced comparable mevalonate yields to expression of $G_0S_0P_0$. $G_1S_2P_2$-competitor1 was identical to $G_1S_2P_2$ with the exception of the addition of a competing PDZ ligand fused to a GST protein co-expressed as the last gene in the pathway operon. $G_1S_2P_2$-competitor1 produced less mevalonate than $G_1S_2P_2$, 29-fold versus 77-fold improvements over no scaffold, respectively. Increased expression of this competing PDZ ligand ($G_1S_2P_2$-competitor2) was achieved with a separate high copy plasmid (ColE1 origin) with $P_{BAD}$ induced to saturation. The fold increase in mevalonate production over no scaffold was further decreased to 9-fold. The necessity of the peptide tags recombined to the pathway enzymes was confirmed with construct $G_1S_2P_2\Delta$ligands. (b) Use of synthetic scaffolds allows higher mevalonate yields to be achieved even with lower expression of pathway enzymes. High expression was achieved with an inducer concentration of 225 nM anhydrotetracycline, while low expression was achieved with 7 nM anhydrotetracycline. Error bars show 1 SD from an average of three separate experiments.

FIG. 10. Domain rearrangements in scaffold architecture dramatically impact pathway flux. For all constructs tested, the mevalonate biosynthesis pathway with recombined interaction domain ligands were expressed by the pTET promoter and the various scaffolds were expressed by the pBAD promoter. $G_0S_0P_0$-GFP provides a control of the same mevalonate biosynthesis pathway with interaction domain peptides recombined to the pathway enzymes but lacking a functional scaffold. Instead, expression of GFP is driven by the pBAD promoter. $G_1S_2P_2$ represents the optimized scaffold with 1, 2, and 2 repeats of GBD, SH3, and PDZ domains, respectively, which produces 77-fold more mevalonate than $G_0S_0P_0$-GFP. $G_1S_1P_2S_1$ and $G_1S_1P_1S_1P_1$ contain the same identity and number of interaction domains as $G_1S_2P_2$ but the arrangement of the HMGS and HMGR-recruiting SH3 and PDZ domains was varied in these scaffold architectures. These showed that scaffold architecture dramatically influences the ability of the scaffold to balance pathway flux.

Figure 11:
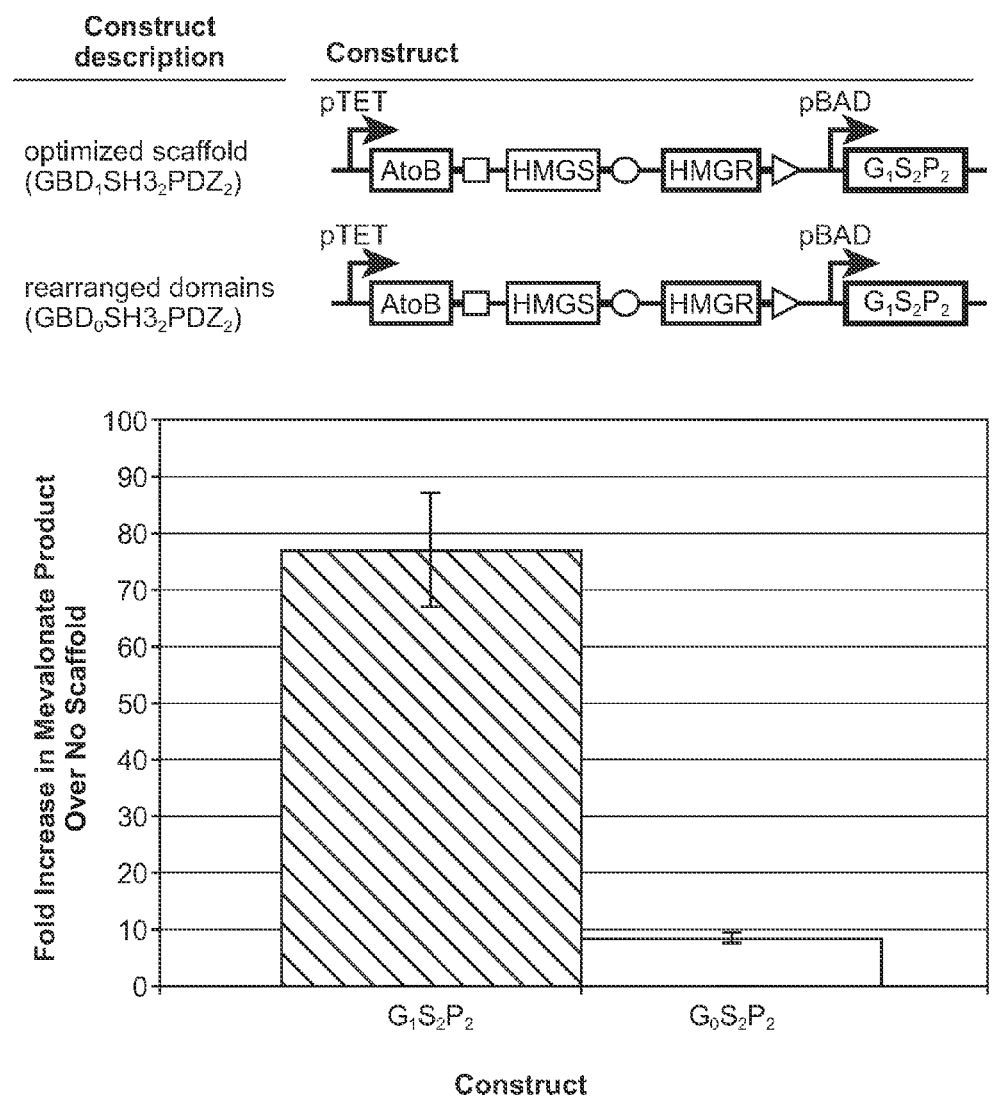
FIG. 11 depicts scalability of scaffold design.

FIG. 11. Probing the scalability of scaffold design. Mevalonate yields with the optimized scaffold $G_1S_2P_2$ that targets all three of the mevalonate biosynthesis enzymes was compared to scaffold $G_0S_2P_2$ that targets only the HMGS/R enzymes. $G_1S_2P_2$, which targets all three enzymes produces a 77-fold higher mevalonate yield than the unscaffolded pathway, whereas $G_0S_2P_2$ only improves mevalonate production 8.5-fold.

FIG. 12. Cell density at saturation is higher for scaffolded pathway at low induction of pathway enzymes but similar at high expression of the pathway enzymes. Scaffolding appears to increase cell viability when the expression of the pathway enzymes is low, but this benefit is lost when pathway expression is increased.

FIG. 13. Scaffolds exhibit glycerol dependence in mevalonate product enhancement. Addition of glycerol as a carbon source would be predicted to increase flux through the mevalonate biosynthetic pathway. Increasing concentrations of glycerol led to modest increases in mevalonate production without scaffold but significant increases when the pathway enzymes were scaffolded with optimized $G_1S_2P_2$. These increases saturated with approximately 4% glycerol. All experiments in this manuscript were conducted with 4% glycerol.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of producing a product or a product precursor of a biosynthetic pathway in a genetically modified host cell, the method comprising culturing a genetically modified host cell under suitable conditions, wherein the genetically modified host cell is genetically modified with one or more nucleic acids comprising:
   a) a nucleotide sequence encoding a scaffold polypeptide of the formula $(X_1)_{n1}(Y_1)(X_2)_{n2}(Y_2)(X_3)_{n3}$, wherein $X_1$, $X_2$, and $X_3$ are different peptide binding elements, wherein each of $n_1$, $n_2$, and $n_3$ is independently an integer from one to about 10, and wherein $Y_1$ and $Y_2$, if present, are linker peptides, wherein the ratio of $n_2$ to $n_3$ provides for at least 25% increased production of the product or product precursor compared to the level of the product or product precursor produced in the corresponding control cell not genetically modified with a nucleic acid comprising a nucleotide sequence encoding the scaffold polypeptide; and
   b) nucleotide sequences encoding at least a first and a second enzyme in a biosynthetic pathway, wherein the first enzyme comprises a first heterologous peptide that binds a first peptide binding element in the scaffold polypeptide, wherein the second enzyme comprises a second heterologous peptide that binds a second peptide binding element, and wherein the first enzyme produces an intermediate that is a substrate for the second enzyme,
   said culturing providing for synthesis of said scaffold polypeptide and said enzymes in the genetically modified host cell, resulting in production of said product or product precursor.

2. The method of claim 1, wherein said biosynthetic pathway is a biosynthetic pathway that converts acetyl-CoA to isopentenyl diphosphate via a mevalonate intermediate, wherein said pathway comprise two or more enzymes that produce an isoprenoid product or an isoprenoid product precursor.

3. The method of claim 2, wherein the isoprenoid product precursor is mevalonate.

4. The method of claim 1, wherein the peptide binding element comprises a protein-protein interaction motif selected from an SH3 domain, a PDZ domain, a GTPase binding domain, a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a Dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, and a bZIP domain.

5. The method of claim 1, wherein the scaffold polypeptide comprises at least three different peptide binding elements, and wherein said at least three peptide binding elements comprise an SH3 domain, a PDZ domain, and a GTPase binding domain.

6. The method of claim 1, wherein the host cell is a prokaryotic cell.

7. The method of claim 1, wherein the host cell is a eukaryotic cell.

* * * * *

SEQUENCE LISTING

<160> NUMBER OF SEQ ID NOS: 37

<210> SEQ ID NO 1
<211> LENGTH: 54
<212> TYPE: PRT
<213> ORGANISM: Artificial Sequence -continued
<220> FEATURE:
<223> OTHER INFORMATION: synthetic polypeptide

<400> SEQUENCE: 1

Tyr Val Arg Ala Leu Phe Asp Phe Asn Gly Asn Asp Glu Glu Asp Leu
1               5                   10                  15

Pro Phe Lys Lys Gly Asp Ile Leu Arg Ile Arg Asp Lys Pro Glu Glu
            20                  25                  30

Gln Trp Trp Asn Ala Glu Asp Ser Glu Gly Lys Arg Gly Met Ile Pro
        35                  40                  45

Val Pro Tyr Val Glu Lys
    50

<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Gly Ser Gly Ser Gly Ser Gly Gly Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

Ala Ala Ala Gly Gly Met
1               5

<210> SEQ ID NO 4
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 4

Ala Ala Ala Gly Gly Met Pro Pro Ala Ala Ala Gly Gly Met
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 5

Ala Ala Ala Gly Gly Met
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

```
<400> SEQUENCE: 6

Pro Pro Ala Ala Ala Gly Gly Met Met
1               5

<210> SEQ ID NO 7
<211> LENGTH: 74
<212> TYPE: PRT
<213> ORGANISM: Artificial Sequence
<220> FEATURE:
<223> OTHER INFORMATION: Synthetic polypeptide

<400> SEQUENCE: 7

Glu Gly Tyr Gln Tyr Arg Ala Leu Tyr Asp Tyr Lys Lys Glu Arg Glu
1               5                   10                  15

Glu Asp Ile Asp Leu His Leu Gly Asp Ile Leu Thr Val Asn Lys Gly
                20                  25                  30

Ser Leu Val Ala Leu Gly Phe Ser Asp Gly Gln Glu Ala Arg Pro Glu
            35                  40                  45

Glu Ile Gly Trp Leu Asn Gly Tyr Asn Glu Thr Thr Gly Glu Arg Gly
        50                  55                  60

Asp Phe Pro Gly Thr Tyr Val Glu Tyr Ile
65                  70

<210> SEQ ID NO 8
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 8

Met Ala Glu Tyr Val Arg Ala Leu Phe Asp Phe Asn Gly Asn Asp Glu
1               5                   10                  15

Glu Asp Leu Pro Phe Lys Lys Gly Asp Ile Leu Arg Ile Arg Asp Lys
                20                  25                  30

Pro Glu Glu Gln Trp Trp Asn Ala Glu Asp Ser Glu Gly Lys Arg Gly
            35                  40                  45

Met Ile Pro Val Pro Tyr Val Glu Lys Tyr
        50                  55

<210> SEQ ID NO 9
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 9

Arg Pro Leu Pro Val Ala Pro
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 10

Pro Pro Pro Ala Leu Pro Pro Lys Lys Arg
1               5                   10
```

```
<210> SEQ ID NO 11
<211> LENGTH: 84
<212> TYPE: PRT
<213> ORGANISM: Artificial Sequence
<220> FEATURE:
<223> OTHER INFORMATION: Synthetic polypeptide

<400> SEQUENCE: 11
```

Glu Ile Thr Leu Glu Arg Gly Asn Ser Gly Leu Gly Phe Ser Ile Ala
 1               5                  10                  15

Gly Gly Thr Asp Asn Pro His Ile Gly Asp Pro Ser Ile Phe Ile
             20                  25                  30

Thr Lys Ile Ile Pro Gly Gly Ala Ala Ala Gln Asp Gly Arg Leu Arg
         35                  40                  45

Val Asn Asp Ser Ile Leu Phe Val Asn Glu Val Asp Val Arg Glu Val
 50                  55                  60

Thr His Ser Ala Ala Val Glu Ala Leu Lys Glu Ala Gly Ser Ile Val
65                  70                  75                  80

Arg Leu Tyr Val

```
<210> SEQ ID NO 12
<211> LENGTH: 87
<212> TYPE: PRT
<213> ORGANISM: Artificial Sequence
<220> FEATURE:
<223> OTHER INFORMATION: Synthetic polypeptide

<400> SEQUENCE: 12
```

Val Met Glu Ile Lys Leu Ile Lys Gly Pro Lys Gly Leu Gly Phe Ser
 1               5                  10                  15

Ile Ala Gly Gly Val Gly Asn Gln His Ile Pro Gly Asp Asn Ser Ile
             20                  25                  30

Tyr Val Thr Lys Ile Ile Glu Gly Gly Ala Ala His Lys Asp Gly Arg
         35                  40                  45

Leu Gln Ile Gly Asp Lys Ile Leu Ala Val Asn Ser Val Gly Leu Glu
     50                  55                  60

Asp Val Met His Glu Asp Ala Val Ala Ala Leu Lys Asn Thr Tyr Asp
65                  70                  75                  80

Val Val Tyr Leu Lys Val Ala
                 85

```
<210> SEQ ID NO 13
<211> LENGTH: 79
<212> TYPE: PRT
<213> ORGANISM: Artificial Sequence
<220> FEATURE:
<223> OTHER INFORMATION: Synthetic polypeptide

<400> SEQUENCE: 13
```

Arg Ile Val Ile His Arg Gly Ser Thr Gly Leu Gly Phe Asn Ile Val
 1               5                  10                  15

Gly Gly Glu Asp Gly Glu Gly Ile Phe Ile Ser Phe Ile Leu Ala Gly
             20                  25                  30

Gly Pro Ala Asp Leu Ser Gly Glu Leu Arg Lys Gly Asp Gln Ile Leu
         35                  40                  45

Ser Val Asn Gly Val Asp Leu Arg Asn Ala Ser His Glu Gln Ala Ala
     50                  55                  60

Ile Ala Leu Lys Asn Ala Gly Gln Thr Val Thr Ile Ile Ala Gln
65                  70                  75

```
<210> SEQ ID NO 14
<211> LENGTH: 82
<212> TYPE: PRT
<213> ORGANISM: Artificial Sequence
<220> FEATURE:
<223> OTHER INFORMATION: Synthetic polypeptide

<400> SEQUENCE: 14

Arg Arg Val Thr Val Arg Lys Ala Asp Ala Gly Gly Leu Gly Ile Ser
 1               5                  10                  15

Ile Lys Gly Gly Arg Glu Asn Lys Met Pro Ile Leu Ile Ser Lys Ile
            20                  25                  30

Phe Lys Gly Leu Ala Ala Asp Gln Thr Glu Ala Leu Phe Val Gly Asp
        35                  40                  45

Ala Ile Leu Ser Val Asn Gly Glu Asp Leu Ser Ser Ala Thr His Asp
    50                  55                  60

Glu Ala Val Gln Ala Leu Lys Lys Thr Gly Lys Glu Val Val Leu Glu
65                  70                  75                  80

Val Lys

<210> SEQ ID NO 15
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 15

Met Leu Gln Arg Arg Val Thr Val Arg Lys Ala Asp Ala Gly Gly
 1               5                  10                  15

Leu Gly Ile Ser Ile Lys Gly Gly Arg Glu Asn Lys Met Pro Ile Leu
            20                  25                  30

Ile Ser Lys Ile Phe Lys Gly Leu Ala Ala Asp Gln Thr Glu Ala Leu
        35                  40                  45

Phe Val Gly Asp Ala Ile Leu Ser Val Asn Gly Glu Asp Leu Ser Ser
    50                  55                  60

Ala Thr His Asp Glu Ala Val Gln Ala Leu Lys Lys Thr Gly Lys Glu
65                  70                  75                  80

Val Val Leu Glu Val Lys Tyr Met Lys Glu Val Ser Pro Tyr Phe Lys
                85                  90                  95

Gly Ser

<210> SEQ ID NO 16
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 16

Ala Asp Ile Gly Thr Pro Ser Asn Phe Gln His Ile Gly His Val Gly
 1               5                  10                  15

Trp Asp Pro Asn Thr Gly Phe Asp Leu Asn Asn Leu Asp Pro Glu Leu
            20                  25                  30

Lys Asn Leu Phe Asp Met Cys Gly Ile Ser Glu
        35                  40
```

```
<210> SEQ ID NO 17
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 17

Lys Glu Arg Pro Glu Ile Ser Leu Pro Ser Asp Phe Glu His Thr Ile
1               5                   10                  15

His Val Gly Phe Asp Ala Val Thr Gly Glu Phe Thr Gly Met Pro Glu
            20                  25                  30

Gln Trp Ala Arg
        35

<210> SEQ ID NO 18
<211> LENGTH: 80
<212> TYPE: PRT
<213> ORGANISM: Artificial Sequence
<220> FEATURE:
<223> OTHER INFORMATION: Synthetic polypeptide

<400> SEQUENCE: 18

Met Thr Lys Ala Asp Ile Gly Thr Pro Ser Asn Phe Gln His Ile Gly
1               5                   10                  15

His Val Gly Trp Asp Pro Asn Thr Gly Phe Asp Leu Asn Asn Leu Asp
            20                  25                  30

Pro Glu Leu Lys Asn Leu Phe Asp Met Cys Gly Ile Ser Glu Ala Gln
        35                  40                  45

Leu Lys Asp Arg Glu Thr Ser Lys Val Ile Tyr Asp Phe Ile Glu Lys
    50                  55                  60

Thr Gly Gly Val Glu Ala Val Lys Asn Glu Leu Arg Arg Gln Ala Pro
65                  70                  75                  80

<210> SEQ ID NO 19
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 19

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu Gly Gly Gly Lys
        35                  40                  45

<210> SEQ ID NO 20
<211> LENGTH: 47
<212> TYPE: PRT
<213> ORGANISM: Artificial Sequence
<220> FEATURE:
<223> OTHER INFORMATION: Synthetic polypeptide
```

```
<400> SEQUENCE: 20

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu Gly Gly Lys
        35                  40                  45

<210> SEQ ID NO 21
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 21

Leu Glu Ile Arg Ala Ala Phe Leu Arg Gln Arg Asn Thr Ala Leu Arg
1               5                   10                  15

Thr Glu Val Ala Glu Leu Glu Gln Glu Val Gln Arg Leu Glu Asn Glu
            20                  25                  30

Val Ser Gln Tyr Glu Thr Arg Tyr Gly Pro Leu Gly Gly Lys
        35                  40                  45

<210> SEQ ID NO 22
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 22

Pro Pro Pro Ala Leu Pro Pro Lys Arg Arg Arg Pro Gly
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 23

Ile Glu Ser Asp Val
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 24

Val Lys Glu Ser Leu Val
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 25

Gly Val Lys Glu Ser Leu Val
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 26

Gly Val Lys Gln Ser Leu Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 27

Gly Val Lys Glu Ser Gly Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 28

Tyr Val Lys Glu Ser Leu Val
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 29

Val Glu Thr Asp Val
1               5

<210> SEQ ID NO 30
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 30

Leu Val Gly Ala Leu Met His Val Met Gln Lys Arg Ser Arg Ala Ile
1               5                   10                  15

His Ser Ser Asp Glu Gly Glu Asp Gln Ala Gly Asp Glu Asp Glu Asp
            20                  25                  30

<210> SEQ ID NO 31
<211> LENGTH: 47
<212> TYPE: PRT
<213> ORGANISM: Artificial Sequence
```

```
<220> FEATURE:
<223> OTHER INFORMATION: Synthetic polypeptide

<400> SEQUENCE: 31

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu Gly Gly Gly Lys
        35                  40                  45

<210> SEQ ID NO 32
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 32

Leu Glu Ile Arg Ala Ala Phe Leu Arg Gln Arg Asn Thr Ala Leu Arg
1               5                   10                  15

Thr Glu Val Ala Glu Leu Glu Gln Glu Val Gln Arg Leu Glu Asn Glu
            20                  25                  30

Val Ser Gln Tyr Glu Thr Arg Tyr Gly Pro Leu Gly Gly Gly Lys
        35                  40                  45

<210> SEQ ID NO 33
<211> LENGTH: 433
<212> TYPE: PRT
<213> ORGANISM: Artificial Sequence
<220> FEATURE:
<223> OTHER INFORMATION: Synthetic polypeptide

<400> SEQUENCE: 33

Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ile Glu
            180                 185                 190
```

```
Ser Gly Ala Phe Thr Ala Glu Ile Val Pro Val Asn Val Thr Arg
            195                 200                 205
Lys Lys Thr Phe Val Phe Ser Gln Asp Glu Phe Pro Lys Ala Asn Ser
210                 215                 220
Thr Ala Glu Ala Leu Gly Ala Leu Arg Pro Ala Phe Asp Lys Ala Gly
225                 230                 235                 240
Thr Val Thr Ala Gly Asn Ala Ser Gly Ile Asn Asp Gly Ala Ala Ala
                    245                 250                 255
Leu Val Ile Met Glu Glu Ser Ala Leu Ala Ala Gly Leu Thr Pro
                260                 265                 270
Leu Ala Arg Ile Lys Ser Tyr Ala Ser Gly Gly Val Pro Pro Ala Leu
                275                 280                 285
Met Gly Met Gly Pro Val Pro Ala Thr Gln Lys Ala Leu Gln Leu Ala
            290                 295                 300
Gly Leu Gln Leu Ala Asp Ile Asp Leu Ile Glu Ala Asn Glu Ala Phe
305                 310                 315                 320
Ala Ala Gln Phe Leu Ala Val Gly Lys Asn Leu Gly Phe Asp Ser Glu
                325                 330                 335
Lys Val Asn Val Asn Gly Gly Ala Ile Ala Leu Gly His Pro Ile Gly
                340                 345                 350
Ala Ser Gly Ala Arg Ile Leu Val Thr Leu Leu His Ala Met Gln Ala
            355                 360                 365
Arg Asp Lys Thr Leu Gly Leu Ala Thr Leu Cys Ile Gly Gly Gly Gln
                370                 375                 380
Gly Ile Ala Met Val Ile Glu Arg Leu Asn Pro Arg Gly Ser Gly Ser
385                 390                 395                 400
Gly Leu Val Gly Ala Leu Met His Val Met Gln Lys Arg Ser Arg Ala
                405                 410                 415
Ile His Ser Ser Asp Glu Gly Glu Asp Gln Ala Gly Asp Glu Asp Glu
                420                 425                 430
Asp

<210> SEQ ID NO 34
<211> LENGTH: 515
<212> TYPE: PRT
<213> ORGANISM: Artificial Sequence
<220> FEATURE:
<223> OTHER INFORMATION: Synthetic polypeptide

<400> SEQUENCE: 34

Met Lys Leu Ser Thr Lys Leu Cys Trp Cys Gly Ile Lys Gly Arg Leu
1               5                   10                  15
Arg Pro Gln Lys Gln Gln Leu His Asn Thr Asn Leu Gln Met Thr
                20                  25                  30
Glu Leu Lys Lys Gln Lys Thr Ala Glu Gln Lys Thr Arg Pro Gln Asn
            35                  40                  45
Val Gly Ile Lys Gly Ile Gln Ile Tyr Ile Pro Thr Gln Cys Val Asn
        50                  55                  60
Gln Ser Glu Leu Glu Lys Phe Asp Gly Val Ser Gln Gly Lys Tyr Thr
65                  70                  75                  80
Ile Gly Leu Gly Gln Thr Asn Met Ser Phe Val Asn Asp Arg Glu Asp
                85                  90                  95
Ile Tyr Ser Met Ser Leu Thr Val Leu Ser Lys Leu Ile Lys Ser Tyr
                100                 105                 110
```

```
Asn Ile Asp Thr Asn Lys Ile Gly Arg Leu Glu Val Gly Thr Glu Thr
            115                 120                 125
Leu Ile Asp Lys Ser Lys Ser Val Lys Ser Val Leu Met Gln Leu Phe
130                 135                 140
Gly Glu Asn Thr Asp Val Glu Gly Ile Asp Thr Leu Asn Ala Cys Tyr
145                 150                 155                 160
Gly Gly Thr Asn Ala Leu Phe Asn Ser Leu Asn Trp Ile Glu Ser Asn
                165                 170                 175
Ala Trp Asp Gly Arg Asp Ala Ile Val Val Cys Gly Asp Ile Ala Ile
                180                 185                 190
Tyr Asp Lys Gly Ala Ala Arg Pro Thr Gly Gly Ala Gly Thr Val Ala
                195                 200                 205
Met Trp Ile Gly Pro Asp Ala Pro Ile Val Phe Asp Ser Val Arg Ala
            210                 215                 220
Ser Tyr Met Glu His Ala Tyr Asp Phe Tyr Lys Pro Asp Phe Thr Ser
225                 230                 235                 240
Glu Tyr Pro Tyr Val Asp Gly His Phe Ser Leu Thr Cys Tyr Val Lys
                245                 250                 255
Ala Leu Asp Gln Val Tyr Lys Ser Tyr Ser Lys Lys Ala Ile Ser Lys
            260                 265                 270
Gly Leu Val Ser Asp Pro Ala Gly Ser Asp Ala Leu Asn Val Leu Lys
            275                 280                 285
Tyr Phe Asp Tyr Asn Val Phe His Val Pro Thr Cys Lys Leu Val Thr
            290                 295                 300
Lys Ser Tyr Gly Arg Leu Leu Tyr Asn Asp Phe Arg Ala Asn Pro Gln
305                 310                 315                 320
Leu Phe Pro Glu Val Asp Ala Glu Leu Ala Thr Arg Asp Tyr Asp Glu
                325                 330                 335
Ser Leu Thr Asp Lys Asn Ile Glu Lys Thr Phe Val Asn Val Ala Lys
                340                 345                 350
Pro Phe His Lys Glu Arg Val Ala Gln Ser Leu Ile Val Pro Thr Asn
            355                 360                 365
Thr Gly Asn Met Tyr Thr Ala Ser Val Tyr Ala Ala Phe Ala Ser Leu
370                 375                 380
Leu Asn Tyr Val Gly Ser Asp Asp Leu Gln Gly Lys Arg Val Gly Leu
385                 390                 395                 400
Phe Ser Tyr Gly Ser Gly Leu Ala Ala Ser Leu Tyr Ser Cys Lys Ile
                405                 410                 415
Val Gly Asp Val Gln His Ile Ile Lys Glu Leu Asp Ile Thr Asn Lys
            420                 425                 430
Leu Ala Lys Arg Ile Thr Glu Thr Pro Lys Asp Tyr Glu Ala Ala Ile
            435                 440                 445
Glu Leu Arg Glu Asn Ala His Leu Lys Lys Asn Phe Lys Pro Gln Gly
450                 455                 460
Ser Ile Glu His Leu Gln Ser Gly Val Tyr Tyr Leu Thr Asn Ile Asp
465                 470                 475                 480
Asp Lys Phe Arg Arg Ser Tyr Asp Val Lys Lys Leu Glu Gly Ser Gly
                485                 490                 495
Ser Gly Ser Gly Ser Gly Pro Pro Ala Leu Pro Pro Lys Arg Arg
            500                 505                 510
Arg Pro Gly
            515
```

<210> SEQ ID NO 35
<211> LENGTH: 514
<212> TYPE: PRT
<213> ORGANISM: Artificial Sequence
<220> FEATURE:
<223> OTHER INFORMATION: Synthetic polypeptide

<400> SEQUENCE: 35

```
Met Val Leu Thr Asn Lys Thr Val Ile Ser Gly Ser Lys Val Lys Ser
 1               5                  10                  15

Leu Ser Ser Ala Gln Ser Ser Ser Gly Pro Ser Ser Ser Ser Ser Glu
            20                  25                  30

Glu Asp Asp Ser Arg Asp Ile Glu Ser Leu Asp Lys Lys Ile Arg Pro
        35                  40                  45

Leu Glu Glu Leu Glu Ala Leu Leu Ser Ser Gly Asn Thr Lys Gln Leu
    50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Gly Ala Cys
        195                 200                 205

Lys Ile Trp Leu Asp Ser Glu Glu Gly Gln Asn Ala Ile Lys Lys Ala
    210                 215                 220

Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
            260                 265                 270

Gln Met Val Glu Glu Tyr Gly Trp Glu Asp Met Glu Val Val Ser Val
        275                 280                 285

Ser Gly Asn Tyr Cys Thr Asp Lys Lys Pro Ala Ala Ile Asn Trp Ile
    290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
            340                 345                 350

Gly Phe Asn Ala His Ala Ala Asn Leu Val Thr Ala Val Phe Leu Ala
        355                 360                 365
```

Leu Gly Gln Asp Pro Ala Gln Asn Val Glu Ser Ser Asn Cys Ile Thr
        370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Thr Val Leu Glu Pro Gln
            405                 410                 415

Gly Ala Met Leu Asp Leu Leu Gly Val Arg Gly Pro His Ala Thr Ala
            420                 425                 430

Pro Gly Thr Asn Ala Arg Gln Leu Ala Arg Ile Val Ala Cys Ala Val
            435                 440                 445

Leu Ala Gly Glu Leu Ser Leu Cys Ala Ala Leu Ala Ala Gly His Leu
450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
            485                 490                 495

Val Thr Cys Ile Lys Ser Gly Ala Pro Gly Ser Gly Val Lys Glu Ser
            500                 505                 510

Leu Val

<210> SEQ ID NO 36
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 36

Met Thr Lys Ala Asp Ile Gly Thr Pro Ser Asn Phe Gln His Ile Gly
1               5                   10                  15

His Val Gly Trp Asp Pro Asn Thr Gly Phe Asp Leu Asn Asn Leu Asp
            20                  25                  30

Pro Glu Leu Lys Asn Leu Phe Asp Met Cys Gly Ile Ser Glu Ala Gln
        35                  40                  45

Leu Lys Asp Arg Glu Thr Ser Lys Val Ile Tyr Asp Phe Ile Glu Lys
    50                  55                  60

Thr Gly Gly Val Glu Ala Val Lys Asn Glu Leu Arg Arg Gln Ala Pro
65                  70                  75                  80

Gly Ser Gly Ser Gly Ser Gly Ser Met Ala Glu Tyr Val Arg Ala
                85                  90                  95

Leu Phe Asp Phe Asn Gly Asn Asp Glu Glu Asp Leu Pro Phe Lys Lys
            100                 105                 110

Gly Asp Ile Leu Arg Ile Arg Asp Lys Pro Glu Glu Gln Trp Trp Asn
        115                 120                 125

Ala Glu Asp Ser Glu Gly Lys Arg Gly Met Ile Pro Val Pro Tyr Val
    130                 135                 140

Glu Lys Tyr Gly Ser Gly Ser Gly Ser Gly Ser Met Leu Gln Arg
145                 150                 155                 160

Arg Arg Val Thr Val Arg Lys Ala Asp Ala Gly Gly Leu Gly Ile Ser
                165                 170                 175

Ile Lys Gly Gly Arg Glu Asn Lys Met Pro Ile Leu Ile Ser Lys Ile
            180                 185                 190

Phe Lys Gly Leu Ala Ala Asp Gln Thr Glu Ala Leu Phe Val Gly Asp
        195                 200                 205

```
Ala Ile Leu Ser Val Asn Gly Glu Asp Leu Ser Ser Ala Thr His Asp
        210                 215                 220
Glu Ala Val Gln Ala Leu Lys Lys Thr Gly Lys Glu Val Val Leu Glu
225                 230                 235                 240
Val Lys Tyr Met Lys Glu Val Ser Pro Tyr Phe Lys Gly Ser
                245                 250

<210> SEQ ID NO 37
<211> LENGTH: 426
<212> TYPE: PRT
<213> ORGANISM: Artificial Sequence
<220> FEATURE:
<223> OTHER INFORMATION: Synthetic polypeptide

<400> SEQUENCE: 37

Met Thr Lys Ala Asp Ile Gly Thr Pro Ser Asn Phe Gln His Ile Gly
  1               5                  10                  15
His Val Gly Trp Asp Pro Asn Thr Gly Phe Asp Leu Asn Asn Leu Asp
             20                  25                  30
Pro Glu Leu Lys Asn Leu Phe Asp Met Cys Gly Ile Ser Glu Ala Gln
         35                  40                  45
Leu Lys Asp Arg Glu Thr Ser Lys Val Ile Tyr Asp Phe Ile Glu Lys
 50                  55                  60
Thr Gly Gly Val Glu Ala Val Lys Asn Glu Leu Arg Arg Gln Ala Pro
 65                  70                  75                  80
Gly Ser Gly Ser Gly Ser Gly Ser Met Ala Glu Tyr Val Arg Ala
             85                  90                  95
Leu Phe Asp Phe Asn Gly Asn Asp Glu Glu Asp Leu Pro Phe Lys Lys
            100                 105                 110
Gly Asp Ile Leu Arg Ile Arg Asp Lys Pro Glu Glu Gln Trp Trp Asn
            115                 120                 125
Ala Glu Asp Ser Glu Gly Lys Arg Gly Met Ile Pro Val Pro Tyr Val
130                 135                 140
Glu Lys Tyr Gly Ser Gly Ser Gly Ser Gly Ser Met Ala Glu Tyr
145                 150                 155                 160
Val Arg Ala Leu Phe Asp Phe Asn Gly Asn Asp Glu Glu Asp Leu Pro
                165                 170                 175
Phe Lys Lys Gly Asp Ile Leu Arg Ile Arg Asp Lys Pro Glu Glu Gln
            180                 185                 190
Trp Trp Asn Ala Glu Asp Ser Glu Gly Lys Arg Gly Met Ile Pro Val
            195                 200                 205
Pro Tyr Val Glu Lys Tyr Gly Ser Gly Ser Gly Ser Gly Gly Ser Met
210                 215                 220
Leu Gln Arg Arg Arg Val Thr Val Arg Lys Ala Asp Ala Gly Gly Leu
225                 230                 235                 240
Gly Ile Ser Ile Lys Gly Gly Arg Glu Asn Lys Met Pro Ile Leu Ile
                245                 250                 255
Ser Lys Ile Phe Lys Gly Leu Ala Ala Asp Gln Thr Glu Ala Leu Phe
            260                 265                 270
Val Gly Asp Ala Ile Leu Ser Val Asn Gly Glu Asp Leu Ser Ser Ala
            275                 280                 285
Thr His Asp Glu Ala Val Gln Ala Leu Lys Lys Thr Gly Lys Glu Val
        290                 295                 300
Val Leu Glu Val Lys Tyr Met Lys Glu Val Ser Pro Tyr Phe Lys Gly
305                 310                 315                 320
```

```
-continued

Ser Gly Ser Gly Ser Gly Gly Ser Met Leu Gln Arg Arg Arg Val Thr
            325                 330                 335

Val Arg Lys Ala Asp Ala Gly Gly Leu Gly Ile Ser Ile Lys Gly Gly
            340                 345                 350

Arg Glu Asn Lys Met Pro Ile Leu Ile Ser Lys Ile Phe Lys Gly Leu
            355                 360                 365

Ala Ala Asp Gln Thr Glu Ala Leu Phe Val Gly Asp Ala Ile Leu Ser
        370                 375                 380

Val Asn Gly Glu Asp Leu Ser Ser Ala Thr His Asp Glu Ala Val Gln
385                 390                 395                 400

Ala Leu Lys Lys Thr Gly Lys Glu Val Val Leu Glu Val Lys Tyr Met
            405                 410                 415

Lys Glu Val Ser Pro Tyr Phe Lys Gly Ser
            420                 425
```